US008349374B2

(12) United States Patent
Woltering et al.

(10) Patent No.: US 8,349,374 B2
(45) Date of Patent: Jan. 8, 2013

(54) **INHIBITION OF ANGIOGENESIS AND DESTRUCTION OF ANGIOGENIC VESSELS WITH EXTRACTS OF NONI JUICE (*MORINDA CITRIFOLIA*)**

(75) Inventors: Eugene A. Woltering, Kenner, LA (US); Conrad A. Hornick, Makawao, HI (US); Amy E. Myers, Austin, TX (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/204,341

(22) Filed: Aug. 5, 2011

(65) Prior Publication Data

US 2011/0293752 A1    Dec. 1, 2011

Related U.S. Application Data

(63) Continuation of application No. 10/488,176, filed as application No. PCT/US02/27579 on Aug. 30, 2002, now Pat. No. 8,012,517.

(60) Provisional application No. 60/316,529, filed on Aug. 31, 2001.

(51) Int. Cl.
*A61K 36/746*      (2006.01)
*A61P 35/04*       (2006.01)
*A61P 35/00*       (2006.01)
*A61P 9/00*        (2006.01)

(52) U.S. Cl. ......... 424/725; 424/769; 424/777; 424/422

(58) Field of Classification Search .................. 424/769, 424/725, 777, 422
See application file for complete search history.

(56) References Cited

U.S. PATENT DOCUMENTS

| 5,288,491 | A  | 2/1994  | Moniz ......................... 424/195.1 |
| 5,773,014 | A  | 6/1998  | Perrier et al. ................. 424/401 |
| 6,214,351 | B1 | 4/2001  | Wadsworth et al. ....... 424/195.1 |
| 6,254,913 | B1 | 7/2001  | Wadsworth et al. .......... 426/481 |
| 6,403,086 | B1 | 6/2002  | Yegorova ..................... 424/94.2 |
| 2002/0168434 | A1 | 11/2002 | Jensen et al. |

OTHER PUBLICATIONS

Solomon, Neil, "Nature's Amazing Healer NONI" 1998 Woodland Publishing (pp. 45, 84 and 92).*

(Continued)

*Primary Examiner* — Aradhana Sasan
(74) *Attorney, Agent, or Firm* — Bonnie J. Davis; John H. Runnels

(57) ABSTRACT

Noni juice and a protein-free, alcohol precipitate of Noni juice inhibited angiogenesis in in vitro human angiogenesis models. When growth medium contained Noni juice at least over the range from about 2.5% to about 33% (by volume), angiogenesis was blocked. Moreover, Noni juice and an ethanol precipitate were able to destroy a pre-existing angiogenic response as well as prevent the development of new vessels. Noni juice was effective in inhibiting the growth of angiogenic vessels from breast cancer explants. It will also be effective in treating cancers and non-cancerous diseases whose response includes an increase in angiogenesis, e.g., retinopathy of prematurity, neovascular glaucoma, diabetic retinopathy, and psoriasis. In an initial experiment, Noni juice was effective in treating lesions associated with psoriasis. The primary antiangiogenic component is believed to be a carbohydrate with a molecular weight less than about 6000 Daltons. In an initial experiment, oral administration of Noni juice appeared to adversely affect the antiangiogenic component(s) in the juice.

3 Claims, 15 Drawing Sheets

OTHER PUBLICATIONS

Ahn, Byung-Zun et al., "Inhibitory Effect of Some Plant Materials Collected in Korea and Vietnam on the Tube-Like Formation of HUVE Cells," Proceedings of the American Association for Cancer Research Annual Meeting, No. 41, pp. 648-649 (Mar. 2000), and 91$^{st}$ Annual Meeting of the American Association for Cancer Research, San Francisco, CA (Apr. 1-5, 2000) ISSN 0197-016X Paragraph 4121.

Bicknell, R., "Vascular targeting and the inhibition of angiogenesis," Annals of Oncology, vol. 5, pp. 45-50 (1994).

Creamer, D. et al., "Overexpression of the angiogenic factor platelet-derived endothelial cell growth factor/thymidine phosphorylase in psoriatic epidermis," Br. J. Dermatol.,vol. 137, pp. 851-855 (1997).

Eerola, A.K. et al., "Tumour infiltrating lymphocytes in relation to tumour angiogenesis, apoptosis," Lung Cancer, vol. 26, pp. 73-83 (1999).

Gasparini, G., "The Rationale and Future Potential of Angiogenesis Inhibitors in Neoplasia," Drugs, vol. 58, No. 1, pp. 17-38 (1999).

Hiramatsu, T. et al., "Induction of normal phenotypes in *ras*-transformed cells by damnacanthal from *Morinda citrifolia*," Cancer Letters, vol. 73, pp. 161-166 (1993).

Hirazumi, A. et al., "An immunomodulatory polysaccharide-rich substance from the fruit juice of *Morinda citrifolia* (Noni) with antitumor activity," Phytotherapy Research, vol. 13, pp. 380-387 (1999).

Hirazumi, A. et al., "Immunomodulation contributes to the Anticancer Activity of *Morinda citrifolia* (Noni) Fruit Juice," Proc. West. Pharmacol. Soc., vol. 39, pp. 7-9 (1996).

Hirazumi, A. et al., "Anticancer Activity of *Morinda citrifolia* (Noni) on Introperitoneally Implanted Lewis Lung Carcinoma in Syngeneic Mice," Proc. West. Pharmacol. Soc., vol. 37, pp. 145-146 (1994).

Kaoumaglo, K. et al., "Effects of three compounds extracted from *Morinda lucida* on *Plasmodium falciparum*," Planta Med., vol. 58, pp. 533-534 (1992).

Liu, G. et al., "Two Novel Glycosides from the Fruits of *Morinda citrofolia* (Noni) Inhibit AP-1 Transactivation and Cell Transformation in the Mouse Epidermal JB6 Cell Line," Cancer Res., vol. 61, pp. 5749-5756 (2001).

Maniotis, A.J. et al., "Vascular channel formation by human melanoma cells in vivo and in vitro: Vasculogenic mimicry," Am. J. Pathol., vol. 155, pp. 739-52 (1999).

Rosen, Lee, "Antiangiogenic Strategies and Agents in Clinical Trails," The Oncologist, vol. 5, supp. 1, pp. 20-27 (2000).

Sikora, Karol, "Cancer Drug Development in the Post-Genomic Age," Current Science, vol. 81, No. 5, pp. 549-554 (2001).

The Merck Index—An Encyclopedia of Chemicals, Drugs, and Biologicals (14$^{th}$ Ed., Ver. 14.3), Edited by: O'Neil, Maryadele J. et al., © 2006, entries for glucuronic acid, galactose, arabinose and rhamnose.

Wang, M. et al., "Novel trisaccharide fatty acid ester identified from the fruits of *Morinda citrifolia* (Noni)," J. Agric. Food Chem., vol. 47, pp. 4880-4882 (1999).

Wenger, F.A. et al., "Tumor size and lymph-node status in pancreatic carcinoma—is there a correlation to the preoperative immune function?," Langenbecks Archives of Surgery, vol. 384, pp. 473-478 (1999).

Zips, Daniel et al., "New Anticancer Agents: in Vitro and in Vivo Evaluation," In Vivo, vol. 19, pp. 1-8 (2005).

* cited by examiner

INHIBITION OF ANGIOGENESIS AND DESTRUCTION OF ANGIOGENIC VESSELS WITH EXTRACTS OF NONI JUICE (*MORINDA CITRIFOLIA*)

This application is a continuation of application Ser. No. 10/488,176, filed Aug. 16, 2004, now U.S. Pat. No. 8,012,517 B2, the entire disclosure of which is incorporated by reference, and which was the United States national stage of international application PCT/US02/27579, filed Aug. 30, 2002, which claims the benefit of the 31 Aug. 2001 filing date of U.S. provisional patent application Ser. No. 60/316,529 under 35 U.S.C. §119(e).

The development of this invention was subject to a contract between the Board of Supervisors of Louisiana State University and Agricultural and Mechanical College, and the United States Department of Veterans Affairs. The United States Government has certain rights in this invention.

TECHNICAL FIELD

This invention pertains to a method to inhibit angiogenesis in cancerous and non-cancerous diseases by use of Noni juice and its active extracts.

BACKGROUND ART

Angiogenesis

In an adult, two types of blood vessels can potentially be found. The normal blood vessel is a resting, quiescent, fully developed vessel. A second form, a proliferating or developing blood vessel, occurs rarely during the normal life cycle (only in early development and reproduction, e.g., menstrual cycle and pregnancy). In contrast, the process of angiogenesis, the proliferation and development of new blood vessels, often occurs in wound healing and in pathological processes, e.g., tumor growth. Angiogenesis is a complex process involving many stages, including extracellular matrix remodeling, endothelial cell migration and proliferation, capillary differentiation, and anastomosis. All detectable solid tumors (tumors over 2 mm in diameter) exploit angiogenesis to supply the needed blood to proliferating tumor cells. Studies have demonstrated that the level of vascularization in a tumor is strongly associated with metastasis in melanoma, breast, and lung carcinomas. See R. Bicknell, "Vascular targeting and the inhibition of angiogenesis," Annals of Oncology, vol. 5, pp. 45-50 (1994).

Angiogenesis inhibitors have been suggested to intervene into neoplastic processes. See G. Gasparini, "The rationale and future potential of angiogenesis inhibitors in neoplasia," Drugs, vol. 58, pp. 17-38 (1999). The inhibitory agents block angiogenesis, thereby causing tumor regression in various types of neoplasia. Known therapeutic candidates include naturally occurring angiogenic inhibitors (e.g., angiostatin, endostatin, platelet factor-4), specific inhibitors of endothelial cell growth (e.g., TNP-470, thalidomide, interleukin-12), agents that neutralize angiogenic molecules (e.g., antibodies to fibroblast growth factor or vascular endothelial growth factor), suramin and its analogs, tecogalan, agents that neutralize receptors for angiogenic factors, agents that interfere with vascular basement membrane and extracellular matrix (e.g., metalloprotease inhibitors, angiostatic steroids), and anti-adhesion molecules (e.g., antibodies such as anti-integrin alpha v beta 3). See L. Rosen, "Antiangiogenic strategies and agents in clinical trials," Oncologist, vol. 5, supplement 1, pp. 20-27 (2000).

Abnormal angiogenesis occurs when improper control of angiogenesis causes either excessive or insufficient blood vessel growth. Excessive blood vessel proliferation favors tumor growth and development of distant metastases, blindness, skin disorders such as psoriasis, and rheumatoid arthritis. Diseases that have been associated with neovascularization include, for example, Crohn's disease, diabetic retinopathy, macular degeneration, sickle cell anemia, sarcoidosis, syphilis, pseudoxanthoma elasticum, Pagets disease, vein occlusion, artery occlusion, carotid obstructive disease, chronic uveitis/vitritis, mycobacterial infections, Lyme disease, systemic lupus erythematosis, psoriasis, retinopathy of prematurity, Eales disease, Bechets disease, infections causing retinitis or choroiditis, presumed ocular histoplasmosis, Bests disease, myopia, optic pits, Stargarts disease, pars planitis, chronic retinal detachment, hyperviscosity syndrome, toxoplasmosis, trauma, and post-laser complications. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. Any disease having a known angiogenic counterpart could potentially be treated with an anti-angiogenic factor, e.g., psoriasis. See D. Creamer et al., "Overexpression of the angiogenic factor platelet-derived endothelial cell growth factor/thymidine phosphorylase in psoriatic epidermis," Br. J. Dermatol., vol. 137, pp. 851-855 (1997).

Angiogenesis is a prominent contributor to solid tumor growth and the formation of distant metastases. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in and around the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. Another complicating factor is that aggressive human melanomas mimic vasculogenesis by producing channels of patterned networks of interconnected loops of extracellular matrix, in which red blood cells, but not endothelial cells, are detected. See A. J. Maniotis et al., "Vascular channel formation by human melanoma cells in vivo and in vitro: Vasculogenic mimicry," Am. J. Pathol., vol. 155, pp. 739-52 (1999). These channels may facilitate perfusion of tumors, independent of perfusion from angiogenesis.

A tumor cannot expand beyond approximately 2 mm without a blood supply to provide nutrients and remove cellular wastes. Tumors in which angiogenesis is important include solid tumors, and benign tumors including acoustic neuroma, neurofibroma, trachoma, and pyogenic granulomas. Inhibiting angiogenesis could halt the growth and potentially lead to regression of these tumors. Angiogenic factors have been reported as being associated with several solid tumors, including rhabdomyosarcoma, retinoblastoma, Ewing sarcoma, neuroblastoma, and osteosarcoma.

Angiogenesis has also been associated with some non-solid tumors, including blood-born tumors such as leukemias, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemias and multiple myelomas.

Antiangiogenic factors inhibit tumor growth beyond 2 mm by inhibiting the angiogenic response and thus inhibiting blood vessel growth to the tumor. Although angiogenesis in a tumor may begin at an early stage, a tumor requires a blood supply to grow much beyond about 2 mm. Up to 2 mm diameter, tumors can survive by obtaining nutrients and oxygen by simple diffusion. Most anti-angiogenic factors are not cytotoxic, i.e., capable of killing the tumor cells directly. Small tumors of a size about 1 mm3 can be effectively inhibited and destroyed by factors, either endogenous or exogenous, that stimulate the immune system. It is generally accepted that once a tumor has reached a critical size, the immunological system is no longer able to effectively destroy the tumor; i.e., there is a negative correlation between tumor size and immune competence. See A. K. Eerola et al., "Tumour infiltrating lymphocytes in relation to tumour angiogenesis, apoptosis," Lung Cancer, vol. 26, pp. 73-83 (1999); and F. A. Wenger et al., "Tumor size and lymph-node status in pancreatic carcinoma—is there a correlation to the preoperative immune function?," Langenbecks Archives of Surgery, vol. 384, pp. 473-478 (1999). Early adjuvant use of an effective anti-angiogenic agent to preclude development of tumor metastases beyond 1 to 2 mm3 may allow more effective tumor attack and control by the body's immunological mechanisms. In addition, prolonged adjuvant use of a non-toxic angiogenic inhibitor may prevent tumor dissemination by blocking the growth of vessels required for the transport of tumor cells that would form metastatic foci.

New antiangiogenic factors are needed, in particular, compounds that not only inhibit new angiogenic growth, but also that degrade existing capillary networks. Very few antiangiogenic factors have been reported to diminish existing capillary networks.

Noni Juice

The Indian mulberry or Noni plant, *Morinda citrifolia* L., is a shrub, or medium size tree that grows in tropical coastal regions. The plant is typically found in the Hawaiian and Tahitian islands. The fruit is juicy, bitter, and dull-yellow or yellowish-white. When fully ripe, the fruit has a pronounced odor similar to that of rancid cheese. Although the fruit has been eaten by several cultures for nutritional and health benefits, the most common use of *Morinda* is as a red and yellow dye source. See U.S. Pat. Nos. 6,214,351; 5,288,491; and 6,254,913. The juice extracted from the Indian mulberry has been used medicinally by several cultures. The juice has been used by herbalists in the treatment of cancer, diabetes, heart trouble, high blood pressure, kidney and bladder disorders. Additionally, the plant itself has been used as a poultice, applied to sores and cuts, and as treatment for boils. See U.S. Pat. No. 5,288,491.

Extracts from the stem, bark and roots of *Morinda* were found to have anti-malarial activity. See K. Kaoumaglo et al., "Effects of three compounds extracted from *Morinda lucida* on *Plasmodium falciparum*," Planta Med., vol. 58, pp. 533-534 (1992). The life span of mice implanted with lung carcinoma cells was prolonged by a series of Noni juice injections beginning one day after implantation of the individual cancer cells. The effect of Noni juice was reported to be due to a polysaccharide-rich substance that stimulated the immune system. The polysaccharide-rich substance was characterized as a gum arabic heteropolysaccharide composed of the sugars glucuronic acid, galactose, arabinose, and ramnose. See A. Hirazumi et al., "An immunomodulatory polysaccharide-rich substance from the fruit juice of *Morinda citrifolia* (Noni) with antitumor activity," Phytotherapy Research, vol. 13, pp. 380-387 (1999). Other polysaccharides have been identified from the fruit of Noni: 2,6-di-O-($\beta$-D-glucopyranosyl)-1-O-octanoyl-$\beta$-D-glucopyranose, rutin, and asperulosidic acid. See M. Wang et al., "Novel trisaccharide fatty acid ester identified from the fruits of *Morinda citrifolia* (Noni)," J. Agric. Food Chem., vol. 47, pp. 4880-4882 (1999). Additionally, damnacanthal, an anthraquinone isolated from a chloroform extract of the roots of Noni, has been shown to inhibit the ras oncogene, and may help suppress activated ras-expressing tumors. See T. Hiramatsu et al., "Induction of normal phenotypes in ras-transformed cells by damnacanthal from *Morinda citrifolia*," Cancer Letters, vol. 73, pp. 161-166 (1993).

DISCLOSURE OF THE INVENTION

We have discovered that Noni juice contains one or more components that inhibit angiogenesis and, that are also capable of degrading existing capillary networks. Noni juice, an ethanol precipitate of Noni juice, and a protein-free extract of Noni juice each individually inhibited angiogenesis in an in vitro human angiogenesis model using a human placental vein disc. When growth medium contained Noni juice at least over the range from about 2.5% to about 33% (by volume), angiogenesis was blocked. Noni juice and the ethanol precipitate of Noni juice were each able to destroy a pre-existing angiogenic capillary network, as well as to prevent the development of new vessels. Noni juice was also effective in blocking capillary development in breast cancer tissue. Noni juice, its ethanol precipitate, or its protein-free extract will be effective in treating cancers, as well as non-cancerous diseases that involve an increase in angiogenesis, e.g., rheumatoid arthritis, retinopathy of prematurity, neovascular glaucoma, diabetic retinopathy, and psoriasis. The primary antiangiogenic component is believed to be a carbohydrate with a molecular weight less than about 6000 Daltons. In an initial experiment, in vivo topical application of a Noni juice composition improved lesions associated with psoriasis on a patient. In an initial experiment, oral administration of Noni juice appeared to adversely affect the antiangiogenic component(s) in the juice.

MODES FOR CARRYING OUT THE INVENTION

EXAMPLE 1

Materials and Methods

Figure 1A:
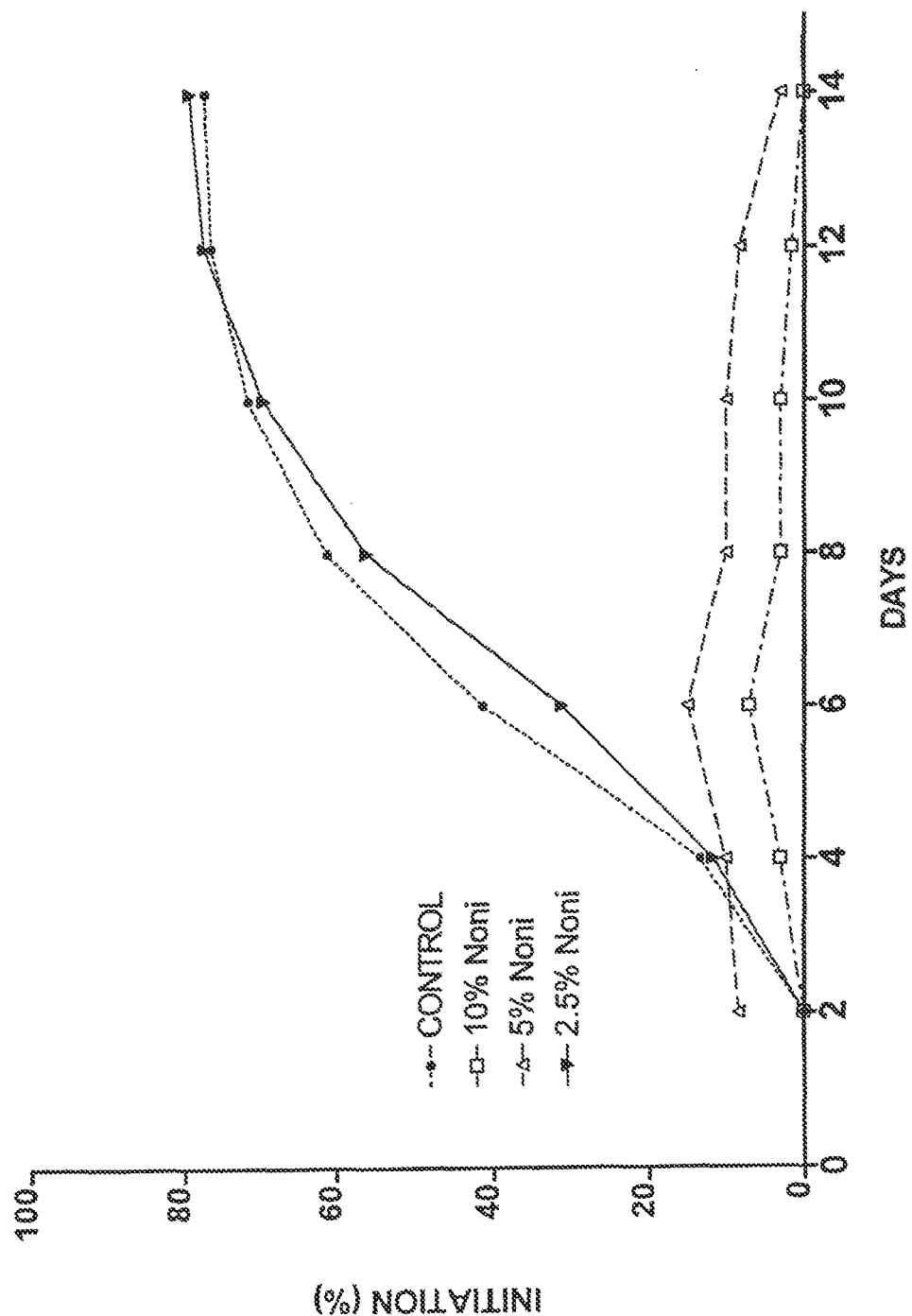
FIG. 1a illustrates the effect of various concentrations of Noni juice (2.5%, 5% and 10%) on the initiation of angiogenesis in human placental vein discs.

The Human Placental Vein Angiogenesis Model: Discarded human placentas were obtained anonymously with prior approval of an Institutional Review Board. The placental veins were dissected free from the placenta and adventitial tissue. The trimmed vein segment was opened longitudinally to produce a flat film of venous tissue of full thickness. Vein discs (2 mm diameter) were created with a sterile skin punch (Miltex Instrument Company, Inc.; Lake Success, N.Y.). The discs were placed into wells of a standard 96-well plate (Corning Inc., Corning, N.Y.). The vein disc harvest was completed within three hours of delivery to optimize endothelial cell viability. Vein discs from a single placenta were distributed equally among all treatment groups to ensure randomization. Each well was preloaded with a human thrombin solution (0.05 IU in 2.0 µl), and allowed to evaporate to dryness before use. All chemicals were purchased from Sigma Chemical Company (St. Louis, Mo.) unless otherwise indicated.

Following the placement of the 2 mm vein disc in the bottom of each thrombin-containing well, the disc was covered with 100 µl of a clot-forming medium, comprising 3 mg/ml fibrinogen and 0.5% ε-amino caproic acid dissolved in Human Placental Vein Angiogenesis Media (HPVAM). HPVAM is made of Medium 199 (Vitrogen Corporation, Carlsbad, Calif.), an antibiotic/antimycotic solution (100 U/ml penicillin, 100 U/ml streptomycin sulfate, and 0.25 µg/ml amphotericinβ; Vitrogen Corporation), and endothelial growth medium (25%) (Vitrogen Corporation). The mixture was allowed to clot by incubating in 5% CO2, 95% air at 37° C. in a humidified incubator. After the medium-containing placental discs had clotted, the vein-containing clot was supplemented with 100 µl HPVAM containing 20% fetal bovine serum (Vitrogen Corporation). The total well volume was 200 µl.

Source of Noni juice: Noni juice was purchased commercially as 100% juice from Herb's Herbs (Kula, Maui, Hi.). Prior to use, the juice was adjusted to pH 7.4 using 50% NaOH, and sterilized using a 0.4 micron Nalgene filter.

Evaluation of Angiogenesis: Visual evaluation of all wells was performed at 20× or 40× magnification with a standardized reference grid by an unbiased observer using an inverted microscope. Every other day, discs were graded using two criteria: the initiation of sprouting vessels (initiation) and the degree of sprouting (angiogenic index). Initiation of an angiogenic response was defined as the development of three or more vessel sprouts around the periphery of the vein disc. Initiation occurred in 50-95% of the wells, usually 4 to 6 days after establishment of the clots. Initiation was expressed as the percent of the total wells plated that indicated an angiogenic response.

The angiogenic index (AI) was defined using a subjective visual rating system. Each disc was visually rated for the development of vessel sprouting in each of four quadrants. Each of the four quadrants for each disc was rated on a 0-4 scale, depending on the number of sprouts (density) and the length of sprouts. Scores for all four quadrants were summed to express the AI, a numerical rating that could range from 0 to 16. A score of zero indicated no vessel growth in any of the four quadrants, while a score of 16 indicated long, dense angiogenic vessel growth in all four quadrants. For most experiments, the AI was expressed as a mean plus/minus a standard error of the mean.

To separate the process of initiation from that of proliferation, the AI was analyzed both with zero AI data points and without zero AI data points. A zero AI indicated that no angiogenic initiation occurred in that disc. This lack of initiation could have been due either to the effect of the experimental compound, to the insensitivity of the vein disc to stimulation in the culture conditions, or to the vein disc not being viable. In previous experiments, we have shown that only a small percent, about 2 to 3%, of vein discs are not viable. (Data not shown) Thus, a graph of AI with zero AI data points indicates the complete angiogenic response of initiation and growth under the experimental conditons. However, a graph of AI without the zero AI data points indicates only growth of the vessels after initiation.

EXAMPLE 2

Inhibitory Effects of Noni Juice on Angiogenesis:

Four separate placentas were used as sources for placental vein discs (PVD) to test the effects of Noni juice on angiogenesis. HPVAM was supplemented with various dilutions of commercial Noni juice to yield four test groups: 33% Noni juice, n=60; 10% Noni, n=120; 5% Noni, n=120; and 2.5% Noni, n=60. The control medium was supplemented with matching concentrations of NaCl (i.e., 33%, 10%, 5%, and 2.5%) to ensure that the observed effects were not due to a difference in concentration of the medium ingredients. Every two days, the medium in each well was replaced, and each well was scored for both initiation of angiogenesis and angiogenic index.

Figure 1B:
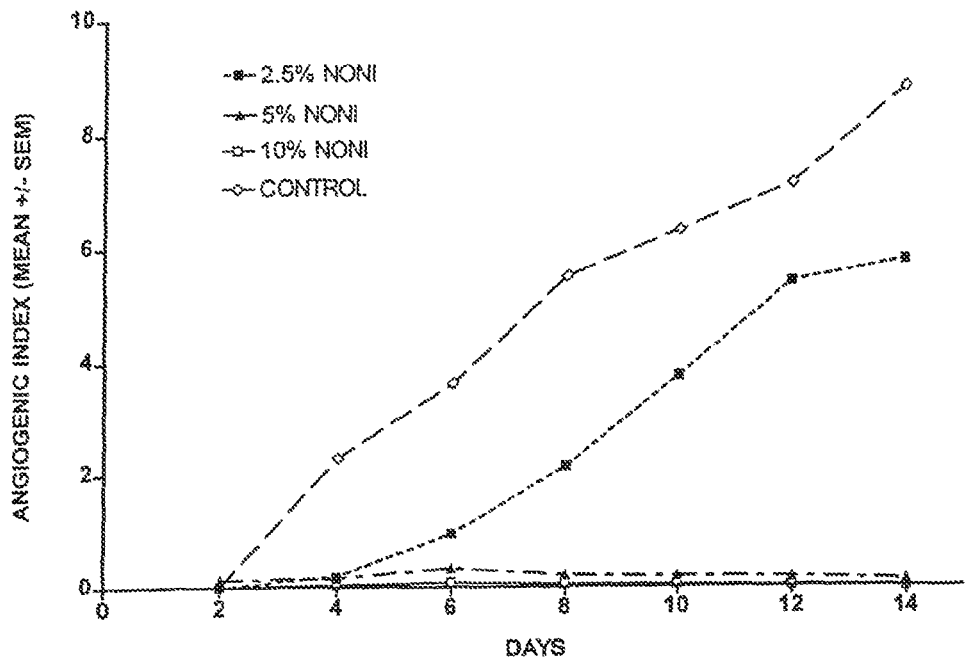
FIG. 1b illustrates the effect of various concentrations of Noni juice (2.5%, 5% and 10%) on angiogenesis (both initiation and proliferation) in human placental vein discs as measured by an angiogenic index.
Figure 1C:
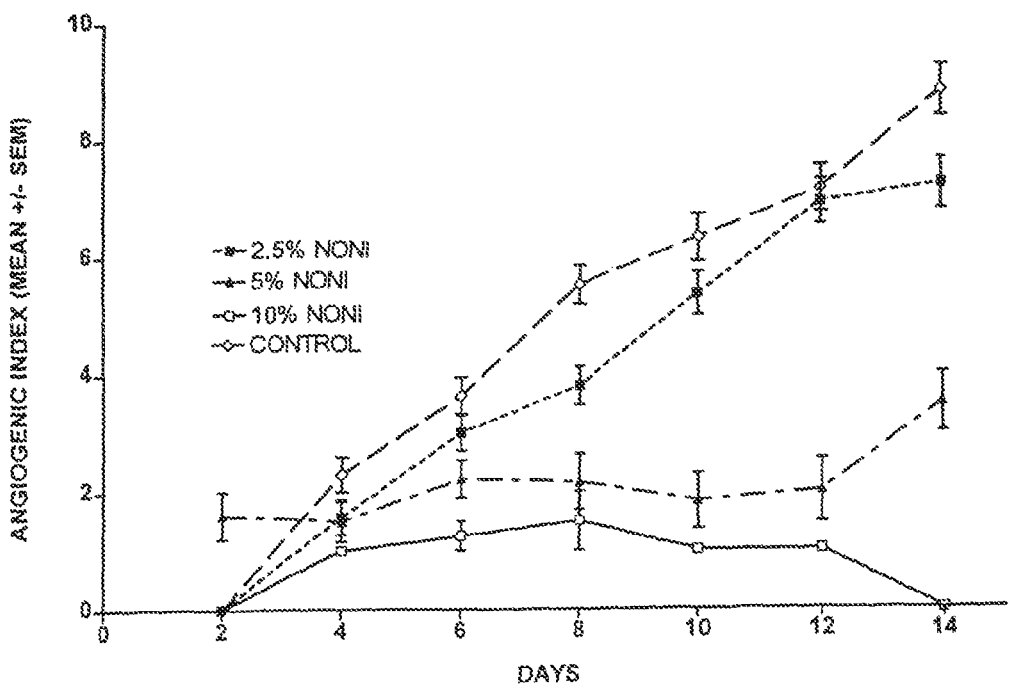
FIG. 1c illustrates the effect of various concentrations of Noni juice (2.5%, 5% and 10%) on angiogenesis in human placental vein discs as measured by an angiogenic index after removing discs with a zero angiogenic index (i.e., discs that never initiated an angiogenic response).

As shown in FIG. 1a, the initiation of angiogenesis was reduced by all concentrations of Noni juice. However, the effect of 2.5% Noni juice was small as compared to that of 5% and 10% Noni juice. The data for 33% Noni juice were not plotted because these vein discs did not show any angiogenesis. When initiation and proliferation were considered together, as measured by the mean AI, a stronger inhibitory effect was seen for 2.5% Noni juice. However, the inhibition was greatest with 5% and 10% Noni. (FIG. 1b). When only proliferation was considered, measured as the mean AI once the zero AI data points are removed, Noni juice at concentrations of at least about 5% had an inhibitory effect. (FIG. 1c).

Based on these results, Noni juice in concentrations greater than about 2.5% is effective in blocking angiogenic initiation and proliferation of the angiogenic network.

EXAMPLE 3

Effects of Noni Juice on Established Capillary Networks

Placental vein discs were derived from two separate placentas to study the effects of Noni juice on established capillary networks. HPVAM was added to the wells and changed every two days. The PVD were allowed to grow for 6 days, at which time a mean AI=3.5 was reached. At this time, the experimental medium was supplemented with 10% Noni juice. Every two days after the addition of Noni juice, the PVD were scored, and the medium was changed as described in Example 1.

Figure 2A:
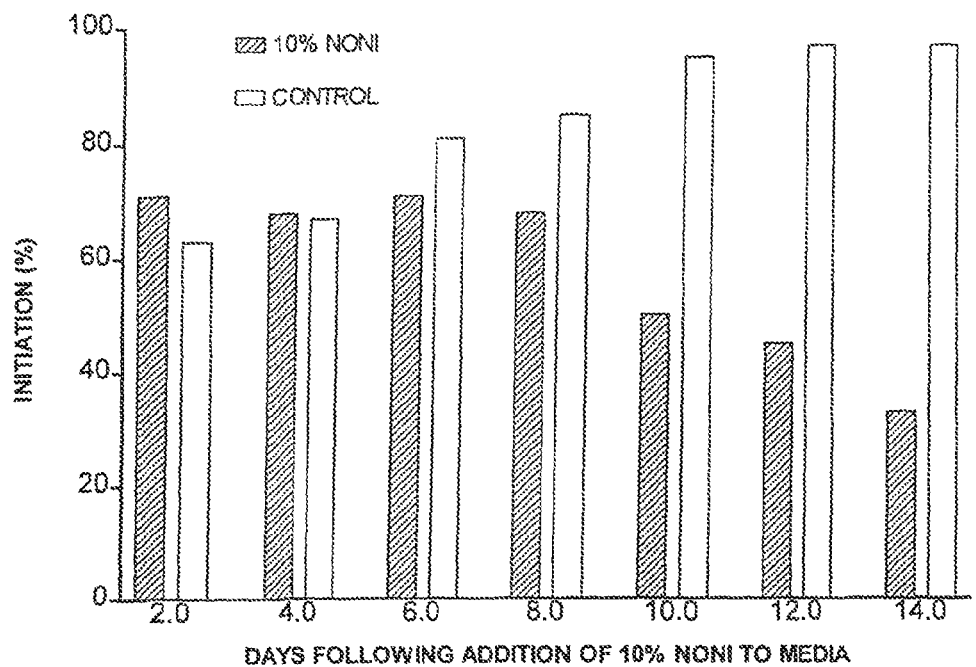
FIG. 2a illustrates the effect of 10% Noni juice on the number of vein discs that exhibited angiogenesis in an established capillary network, a six-day angiogenic growth in human placental vein discs under standard conditions.
Figure 2B:
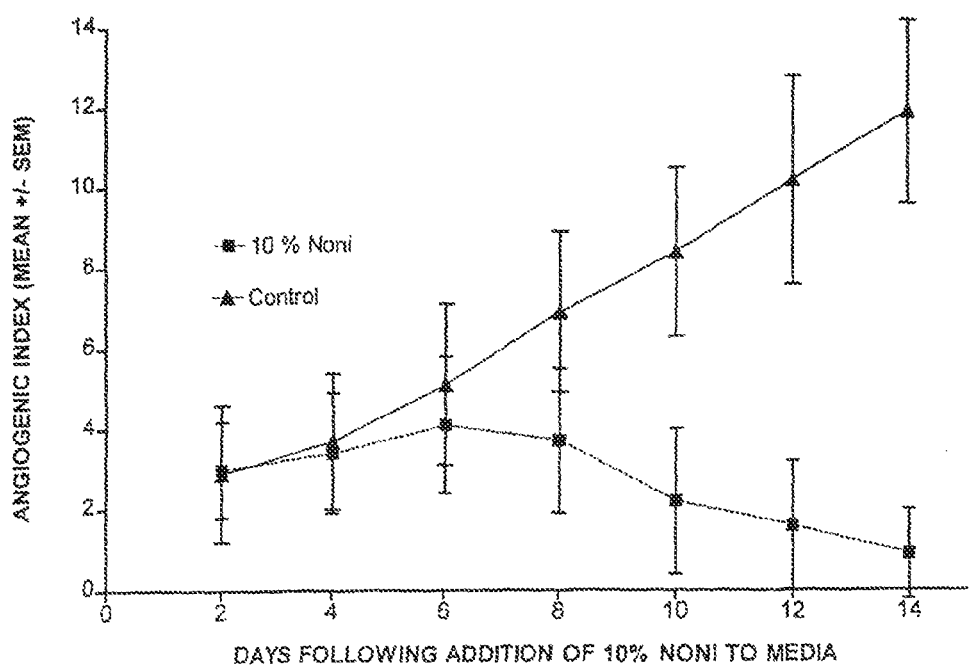
FIG. 2b illustrates the effect of 10% Noni juice on angiogeneic development as measured by an angiogenic index in an established capillary network, a six-day angiogenic growth in human placental vein discs under standard conditions.

The number of wells with angiogenic vessels decreased upon addition of 10% Noni following six days of disc growth in standard medium. (FIG. 2a). In addition, both initiation and proliferation, measured as the mean AI, decreased after 10% Noni juice was added. (FIG. 2b). In both FIGS. 2a and 2b, the x-axis represents days following the initiation of the Noni treatment.

EXAMPLE 4

Effects of Storage Temperature on Noni Juice Efficacy

To test for the effect of storage temperature on Noni juice angiogenic efficacy, two separate placentas were used. Three separate sets, each with 60 PVD, were treated with 10% Noni juice that was made from a stock 100% Noni juice that was stored prior to dilution under one of the following conditions: (1) frozen and thawed three consecutive times; (2) heated to boiling for 10 min; and (3) stored at 4° C. A control group was also established using 10% NaCl. The PVD were scored, and the media changed every two days.

Figure 3A:
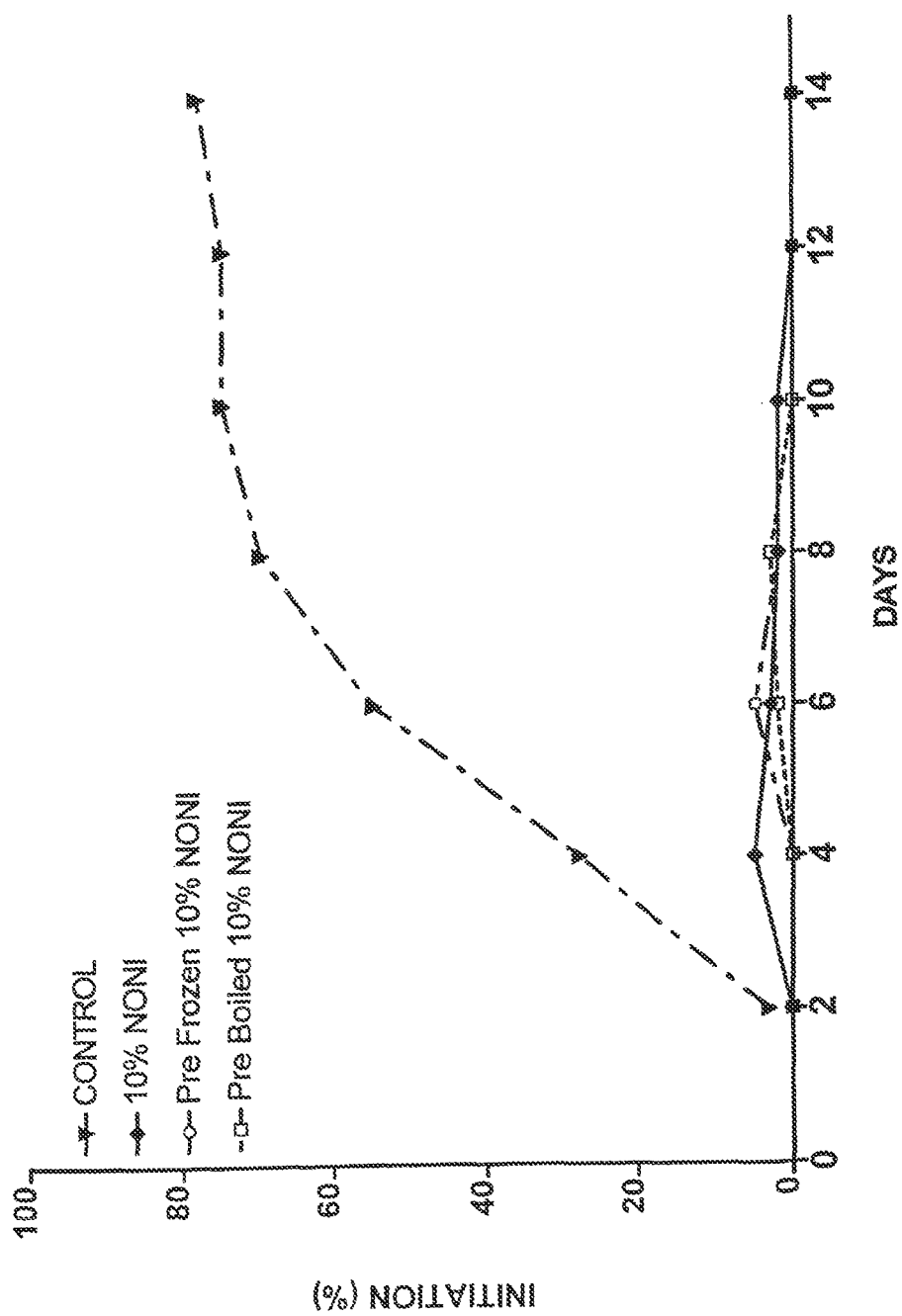
FIG. 3a illustrates the effect of 10% Noni juice, after being frozen or boiled, on the initiation of angiogenesis in human placental vein discs.
Figure 3B:
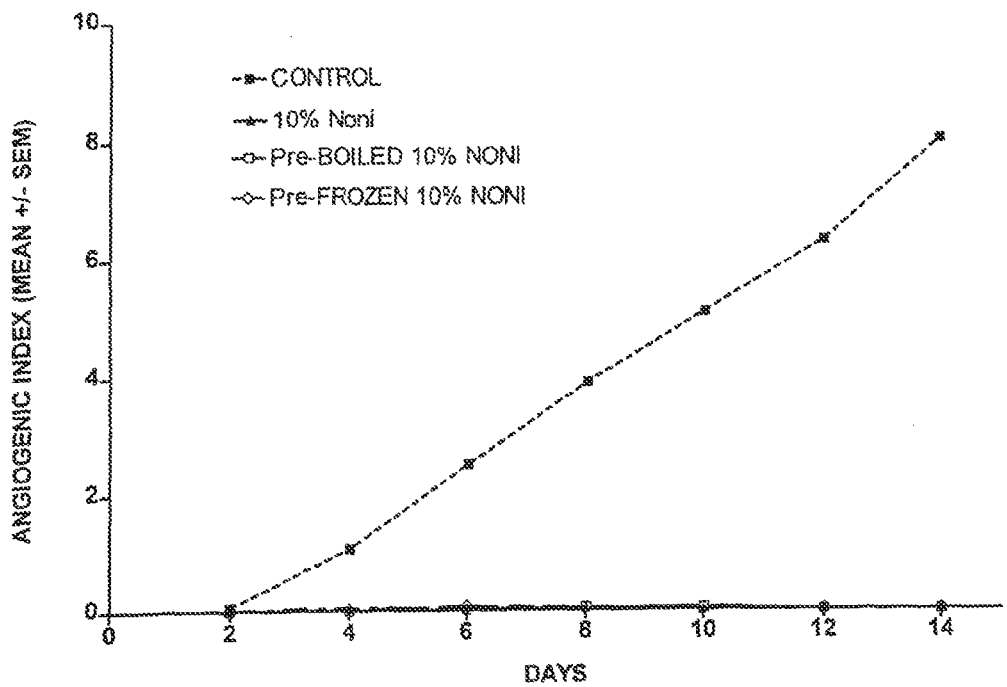
FIG. 3b illustrates the effect of 10% Noni juice, after being frozen or boiled, on the initiation and proliferation of angiogenesis in human placental vein discs as measured by the angiogenic index.
Figure 3C:
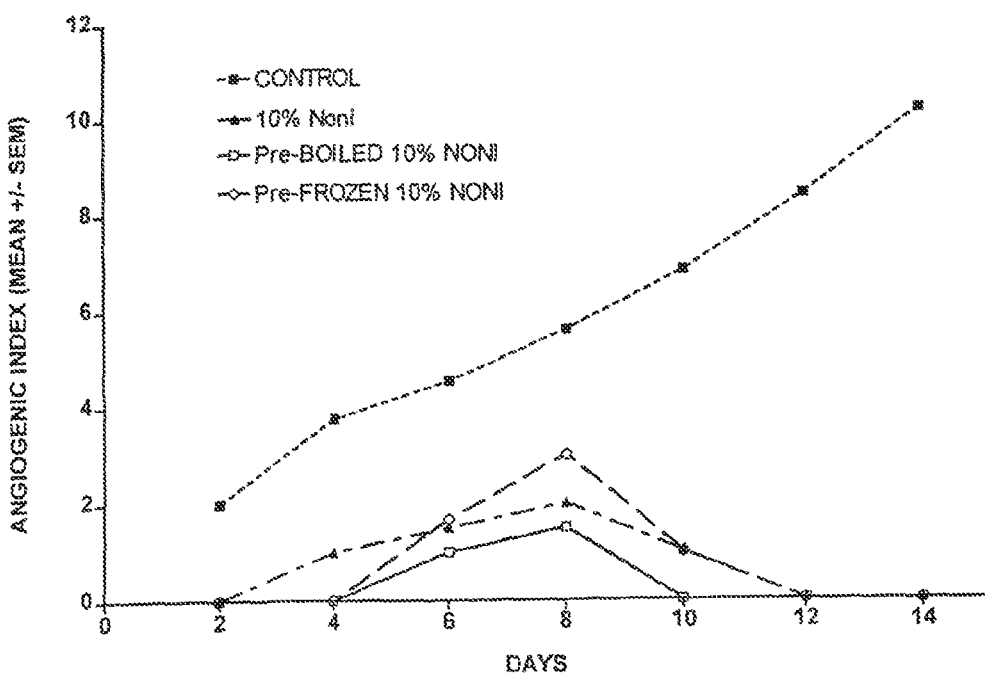
FIG. 3c illustrates the effect of 10% Noni juice, after being frozen or boiled, on the proliferation of angiogenesis in human placental vein discs as measured by the angiogenic index, after removing discs with a zero angiogenic index (i.e., discs that never initiated an angiogenic response).

As shown in FIGS. 3a, 3b, and FIG. 3c, neither freezing nor boiling destroyed the inhibitory effect of Noni juice on either the initiation or proliferation of angiogenesis.

EXAMPLE 5

Ethanol Precipitation of Noni Juice

An ethanol precipitate of Noni juice was prepared by mixing 100 ml of Noni juice with 300 ml absolute ethanol, and then centrifuging for 15 min at 3000 rpm. The supernatant was decanted, and the pellet resuspended in 25 ml deionized water. To this solution, was added 75 ml ethanol for a second extraction. The solution was again centrifuged for 15 min at 3000 rpm. After discarding the supernatant, the pellet was lyophilized for 24 hr. The brown, crystalline pellet was ground to a fine powder. Approximately 1 gm of powder was recovered for each 100 ml of Noni juice.

EXAMPLE 6

Efficacy of the Ethanol Precipitate of Noni Juice

To test the effectiveness of the ethanol precipitate of Noni juice, two separate placentas were used to generate the PVD. Approximately 1 gm Noni precipitate from Example 5 was reconstituted in 100 ml Medium 199 to make a solution whose concentration (of components from the precipitate) was approximately equal to that of 100% Noni juice. The solution was allowed to sit overnight at 32° C. This solution was diluted with Medium 199 to make three concentrations equivalent to 2.5%, 5% and 10% Noni juice. A positive control group was established using a heparin-steroid (21-phosphate hydrocortisone) mixture (300 µg/ml and 350 µg/ml, respectively), which was previously found to reduce angiogenesis by 30 to 40%. See S. P. Jung et al., "Inhibition of human angiogenesis with heparin and hydrocortisone," Angiogenesis, vol. 4, in press (2001). An untreated control group was also established. The number of PVDs in each group was 60. The PVDs were scored, and the media changed every two days.

Figure 4A:
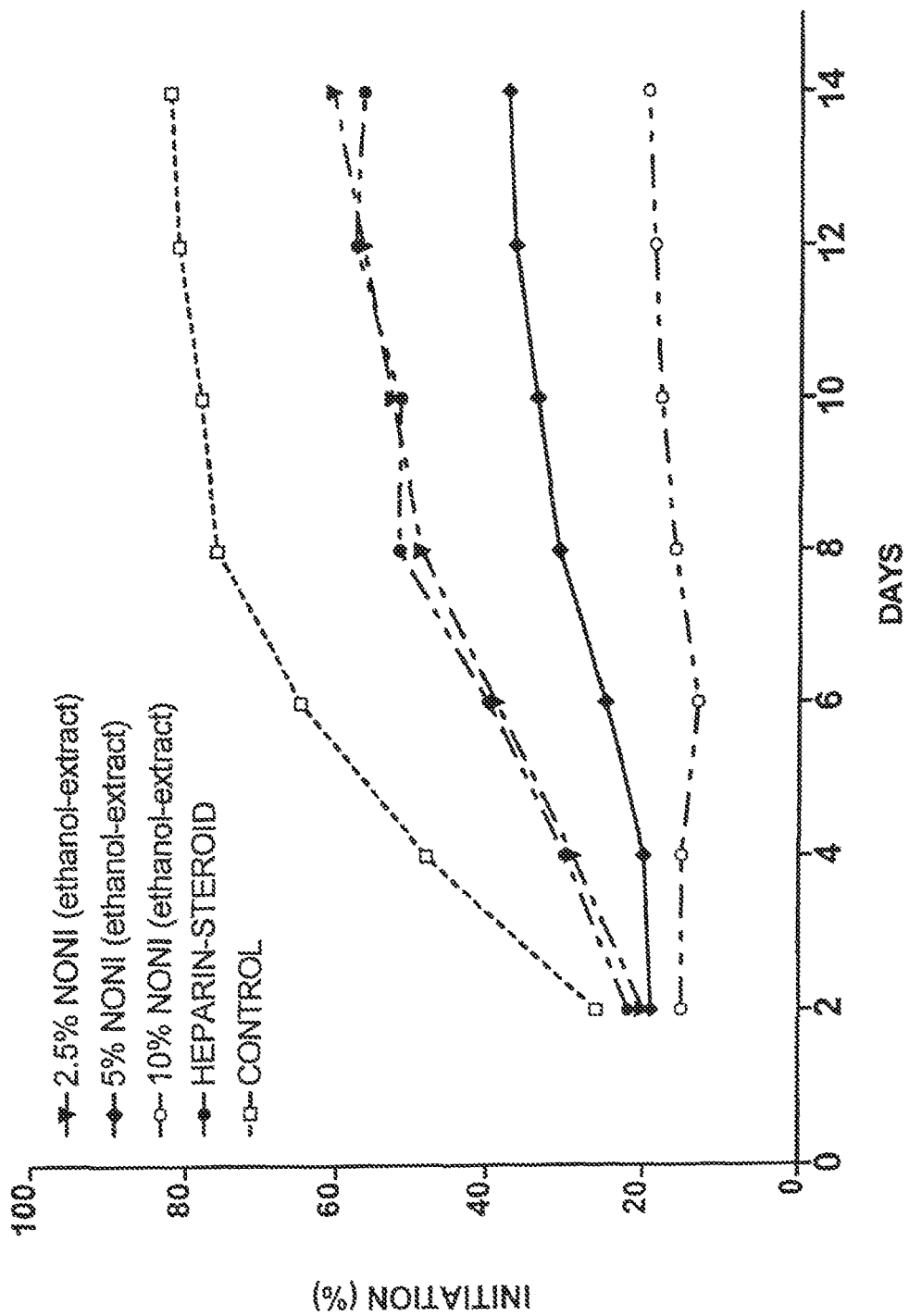
FIG. 4a illustrates the effect of a reconstituted Noni ethanol precipitate at concentrations of 2.5%, 5% and 10% and a heparin-steroid (H-S) combination on the initiation of angiogenesis in human placental vein discs.
Figure 4B:
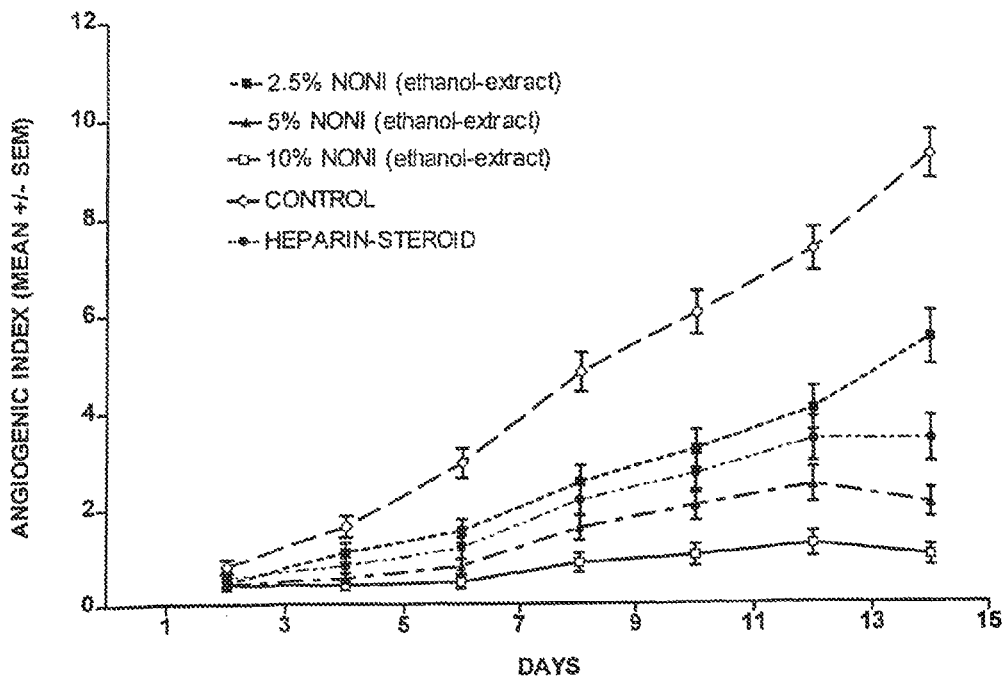
FIG. 4b illustrates the effect of a reconstituted Noni ethanol precipitate at concentrations of 2.5%, 5% and 10% and a heparin-steroid (H-S) combination on the initiation and proliferation of angiogenesis in human placental vein discs as measured by the angiogenic index.
Figure 4C:
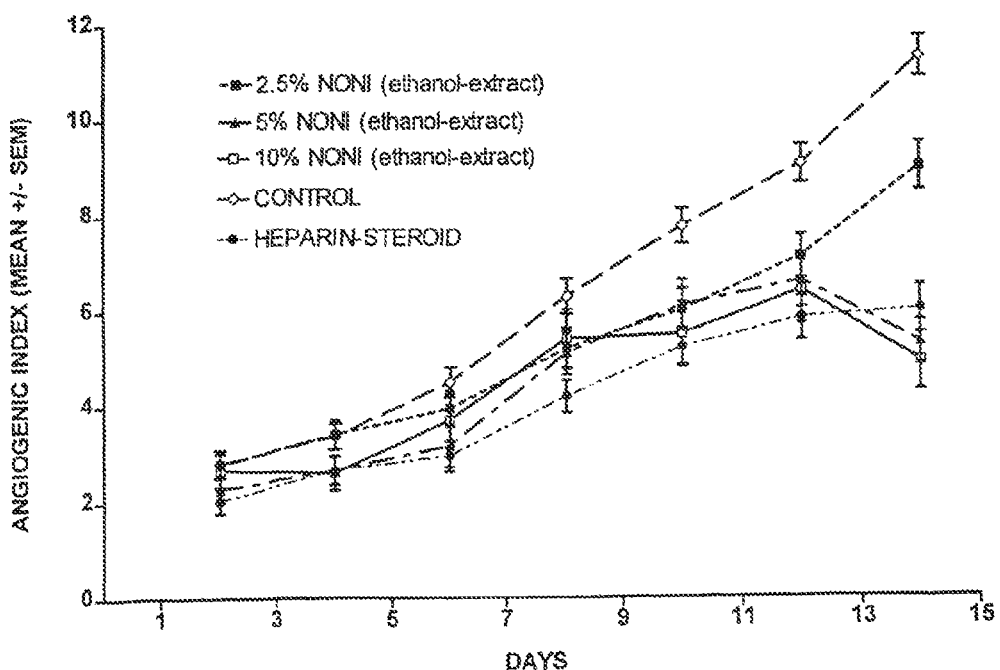
FIG. 4c illustrates the effect of a reconstituted Noni ethanol precipitate at concentrations of 2.5%, 5% and 10% and a heparin-steroid (H-S) combination on the proliferation of angiogenesis in human placental vein discs as measured by the angiogenic index, after removing discs with a zero angiogenic index (i.e., discs that never initiated an angiogenic response).

As shown in FIGS. 4a, 4b, and 4c, both the initiation and proliferation of angiogenic vessels were inhibited by the Noni precipitate at concentrations comparable to the intact Noni juice. In this experiment, only the inhibitory effect of 2.5% Noni juice was similar to that of the heparin-steroid control.

The other concentrations showed greater inhibition. This experiment indicated that a primary anti-angiogenic factor in Noni juice separates in an ethanol precipitate.

EXAMPLE 7

Effect of the Ethanol Precipitate of Noni Juice on Established Capillary Networks To test the effect of the ethanol precipitate of Noni juice on established capillary networks, two separate placentas were used to generate PVDs. The ethanol precipitate was prepared as in Example 5, and solutions of 10%, 5% and 2.5% were generated as described in Example 6. PVDs with standard HPVAM were allowed to become angiogenic for 6 days, changing the media every two days. By the sixth day, the mean AI was 4.0. At this time, the HPVAM was supplemented with one of the three Noni concentrations, a heparin-steroid medium (as described in Example 6), or control medium. The PVDs were scored, and the medium changed every two days.

Figure 5:
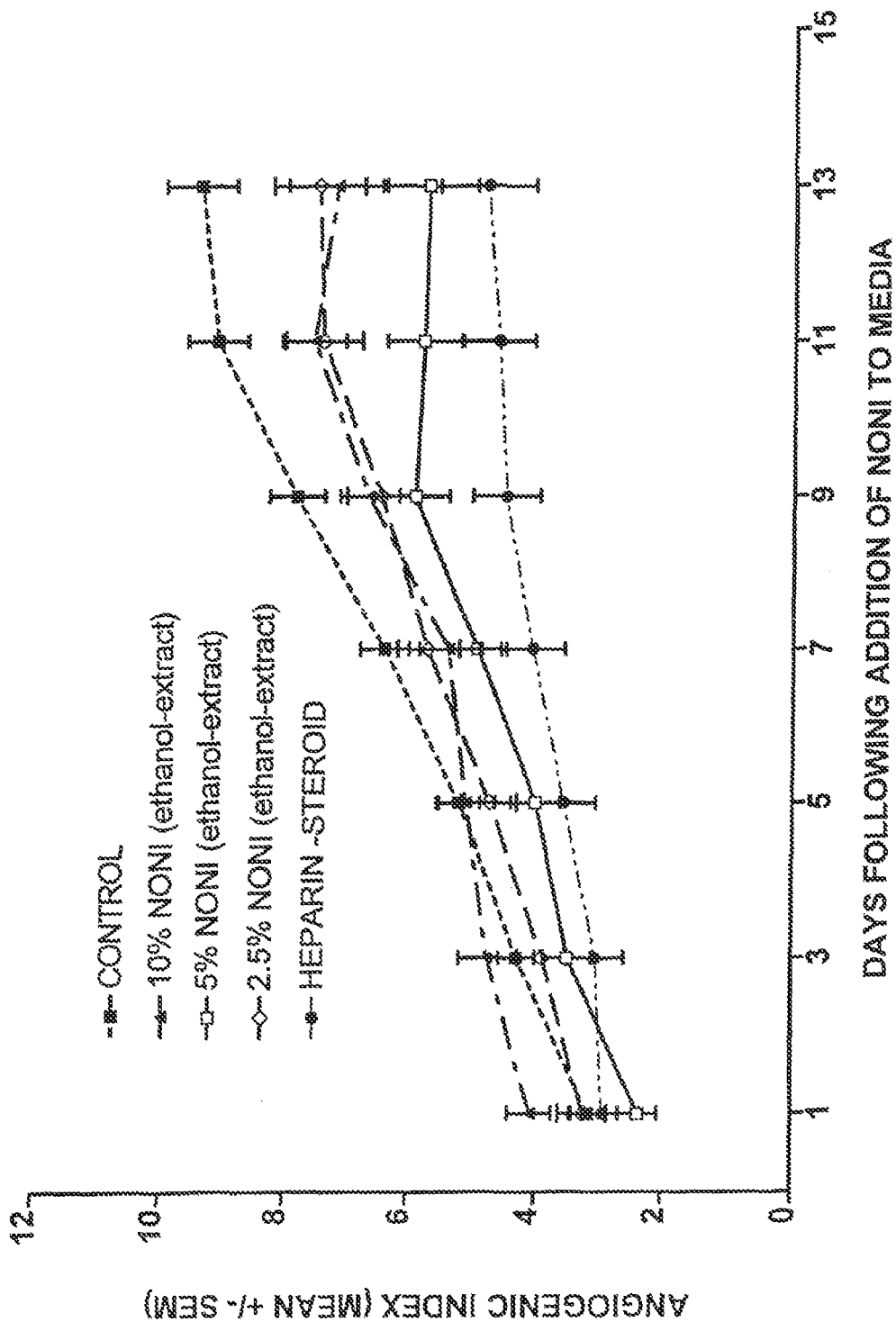
FIG. 5 illustrates the effect of a reconstituted Noni ethanol precipitate at concentrations of 2.5%, 5% and 10% and a heparin-steroid (H-S) combination on the number of vein discs that exhibited angiogenesis in an established capillary network, a six-day angiogenic growth in human placental vein discs under standard conditions.

As shown in FIG. 5, proliferation of angiogenesis in established capillary networks was inhibited by the Noni ethanol precipitate. The x-axis in FIG. 5 represents the number of days following the initiation of Noni treatment. However, the effect was less than the inhibition seen for a 10% Noni solution made from the unextracted juice. (See FIG. 2b) This experiment indicates that some effectiveness of Noni juice on established capillary networks was lost in the ethanol extraction.

EXAMPLE 8

Effectiveness of Other Extracts of Noni Juice

Figure 6A:
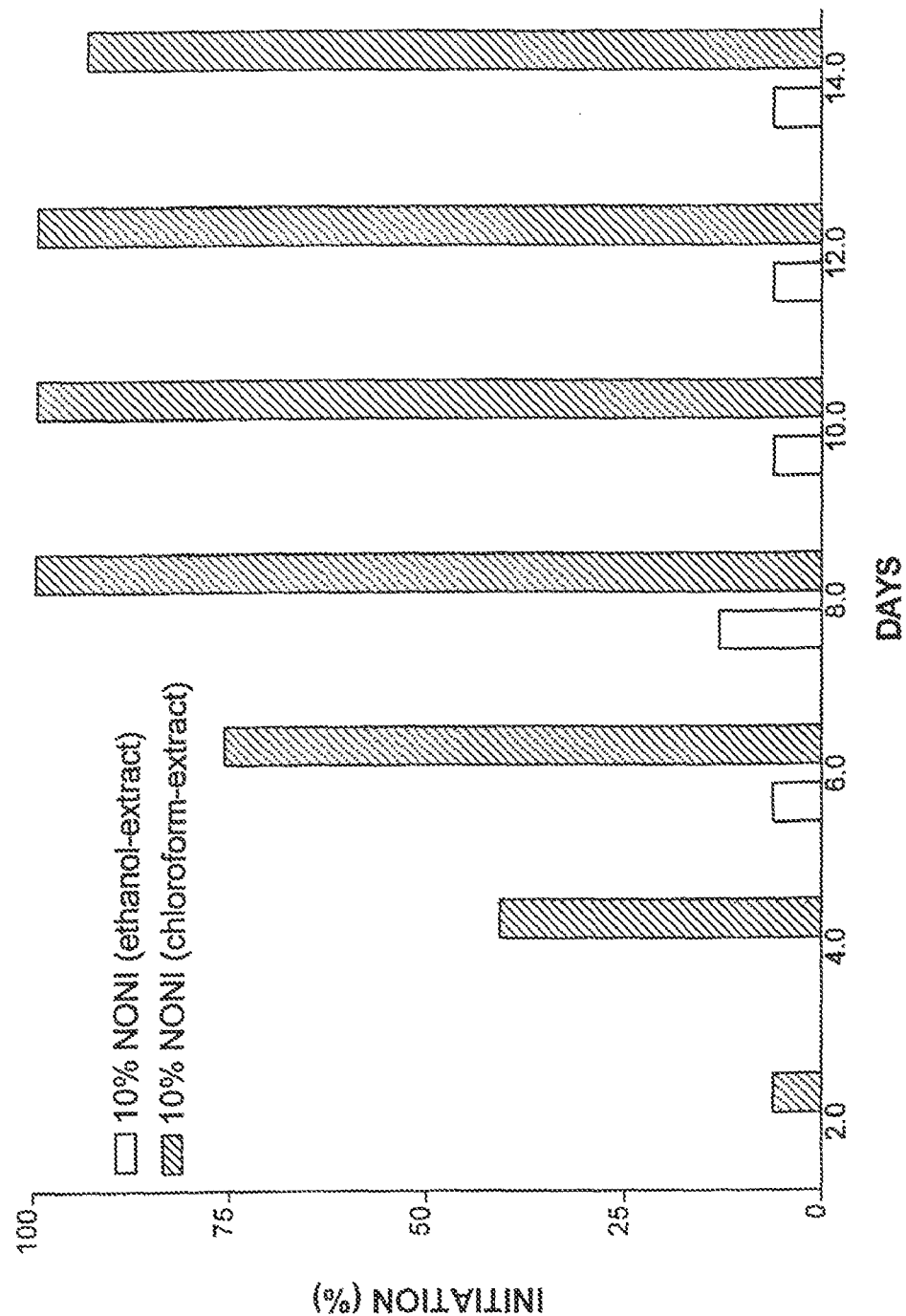
FIG. 6a illustrates the effect of an ethanol extract and a chloroform extract of Noni juice on the initiation of angiogenesis in human placental vein discs.
Figure 6B:
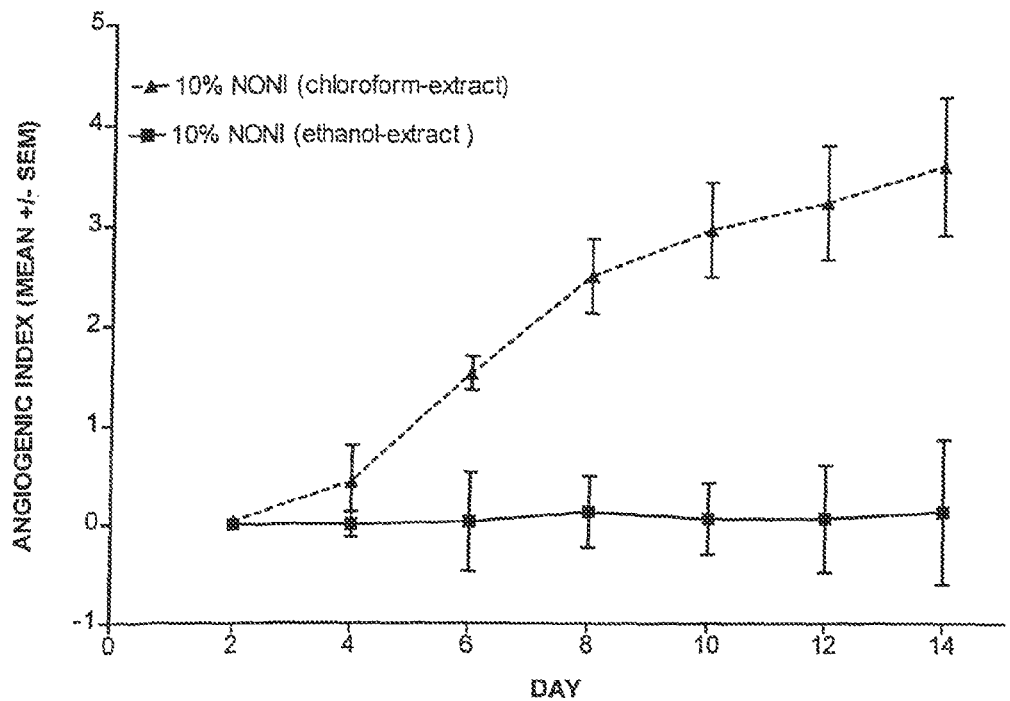
FIG. 6b illustrates the effect of an ethanol extract and a chloroform extract of Noni juice on the initiation and proliferation of angiogenesis in human placental vein discs as measured by the angiogenic index.
Figure 6C:
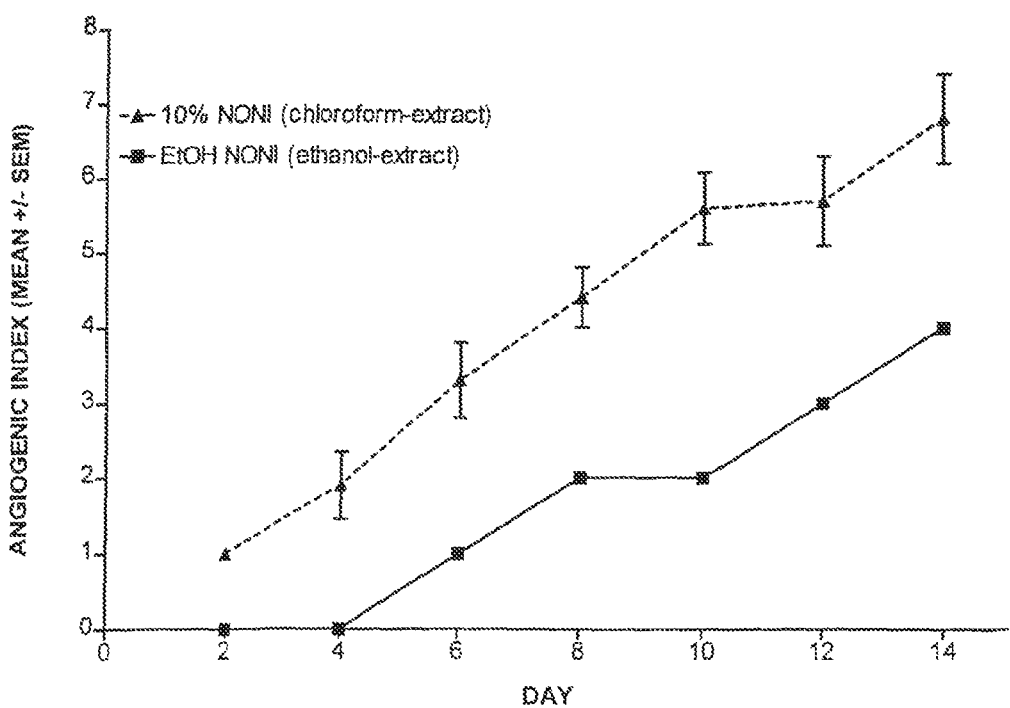
FIG. 6c illustrates the effect of an ethanol extract and a chloroform extract of Noni juice on the proliferation of angiogenesis in human placental vein discs as measured by the angiogenic index, after removing discs with a zero angiogenic index (i.e., discs that never initiated an angiogenic response).

Chloroform-Ethanol Extraction. Noni juice (10 ml) was extracted with 16.67 ml of a chloroform-ethanol volumetric mixture (ratio 1:2). The mixture was vortexed, and left at room temperature. After 30 min, 5.56 ml chloroform was added. The mixture was again vortexed, then centrifuged at 2000 g for 15 min and allowed to stand overnight at 4° C. The mixture partitioned into two phases: chloroform as the lower phase and ethanol as the upper. PVD explants were treated with either the upper or lower phase following drying and reconstituting in Medium 199 to achieve a concentration approximately equal to a 10% solution of native Noni juice, as generally described in Example 6. The results demonstrated that the factor responsible for both the reduction of angiogenic initiation and the inhibition of angiogenic proliferation was found primarily in the ethanol fraction, but not in the chloroform fraction. See FIGS. 6a, 6b, and 6c. This demonstrated that the antiangiogenic component is not damnacanthal or another anthraquinone that would be extracted with chloroform.

n-Butanol Extraction. Noni juice (10 ml) was extracted with 30 ml n-Butanol, and the mixture mixed for 10 min. The mixture was then centrifuged for 15 min at 2000 g, and the resulting precipitate collected. In the supernatant, two resulting fractions (a top butanol fraction and a lower aqueous fraction) were separated, and both brought to 50 ml with n-butanol for a second extraction and centrifuged for 10 min at 2000 g. The resulting pellets were decanted, lyophilized, and reconstituted in Medium 199 to reach a concentration (of components from the precipitate) approximately equal to that of 5% native Noni juice. Both fractions were then tested on the PVD explants. The results indicated that the active fraction was precipitated with the addition of butanol, but that the precipitation was incomplete with the initial butanol addition.

Figure 7A:
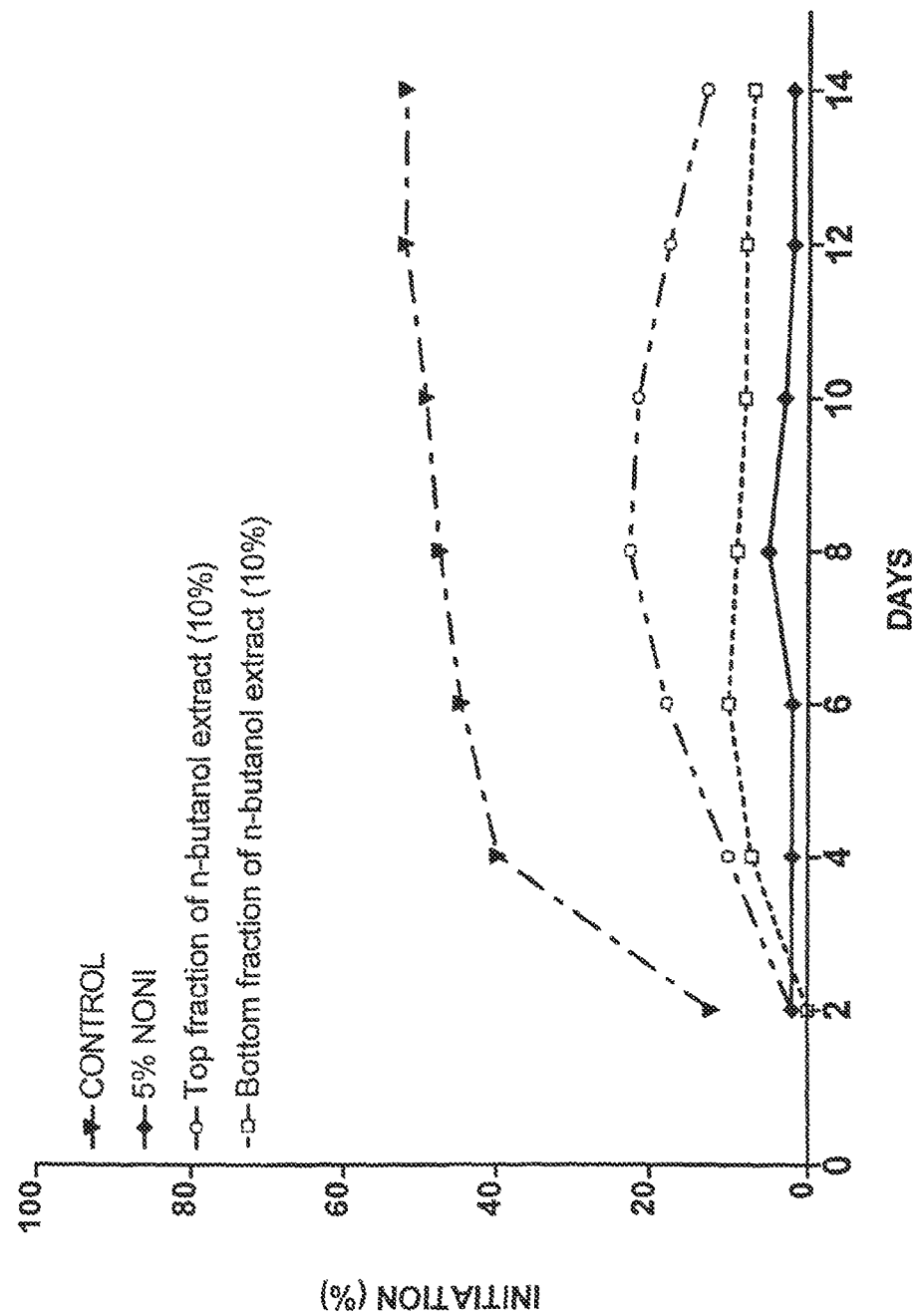
FIG. 7a illustrates the effect of an n-butanol extract of Noni juice on the initiation of angiogenesis in human placental vein discs.
Figure 7B:
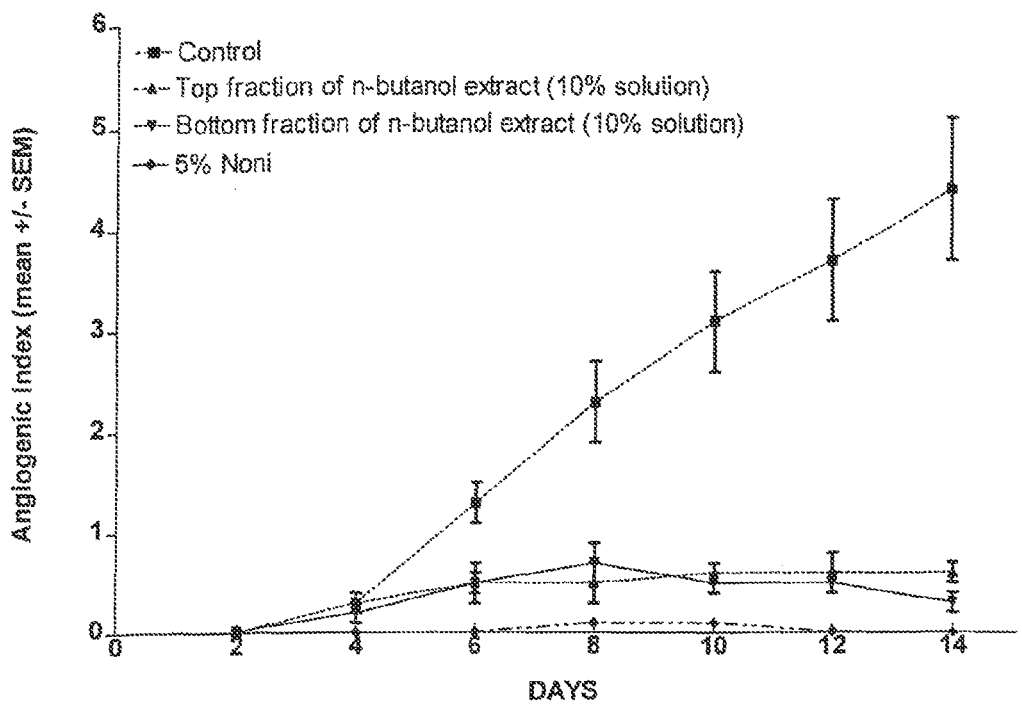
FIG. 7b illustrates the effect of an n-butanol extract of Noni juice on the initiation and proliferation of angiogenesis in human placental vein discs as measured by the angiogenic index.
Figure 7C:
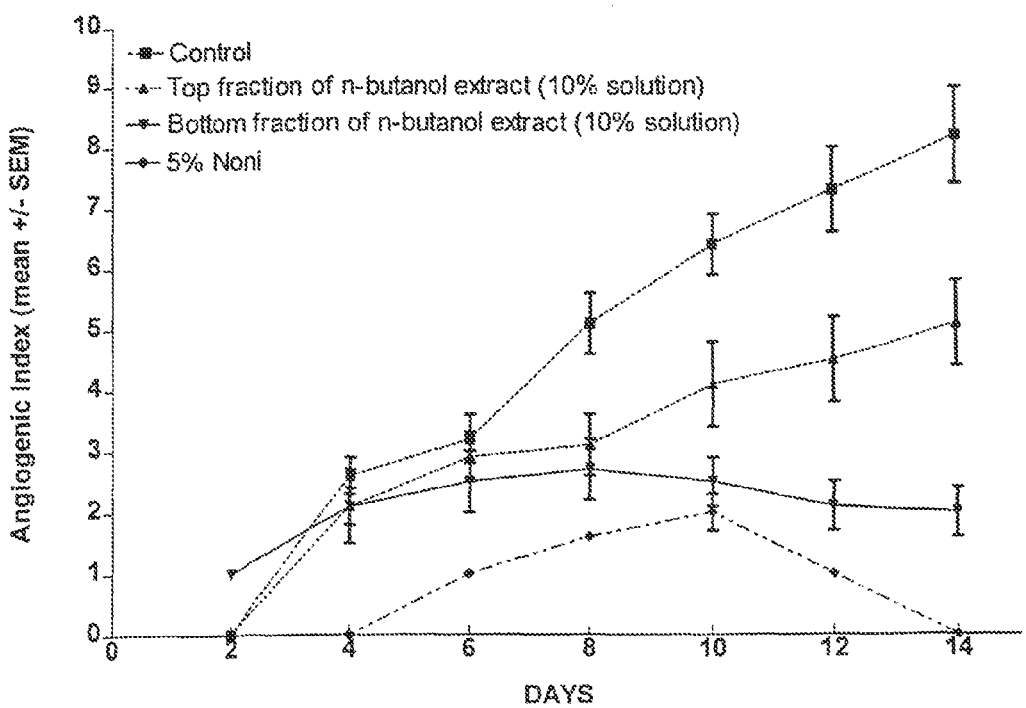
FIG. 7c illustrates the effect of an n-butanol extract of Noni juice on the proliferation of angiogenesis in human placental vein discs as measured by the angiogenic index, after removing discs with a zero angiogenic index (i.e., discs that never initiated an angiogenic response).

FIGS. 7a, 7b, and 7c indicate that both fractions retained the ability to inhibit both initiation and proliferation of angiogenesis.

Figure 8:
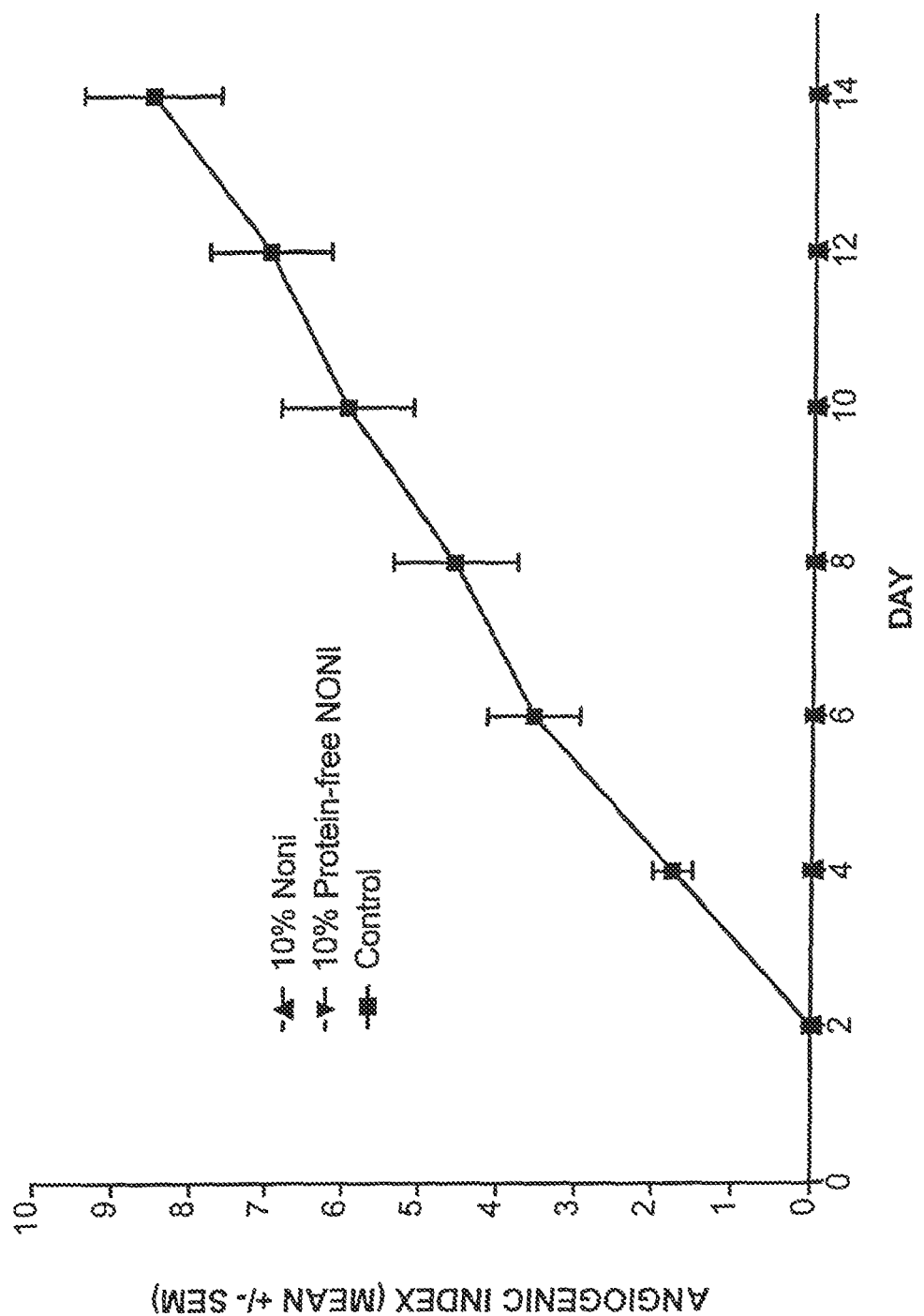
FIG. 8 illustrates the effect of a protein-free extract of Noni juice on the initiation and proliferation of angiogenesis in human placental vein discs as measured by the angiogenic index.

Protein removal from Noni juice: Protein was precipitated from Noni juice by the addition of 10.8% trichloroacetic acid (TCA) and 1 mg/ml bovine serum albumin (BSA) to 10 ml Noni juice. The mixture was refrigerated for 30 min, then centrifuged for 15 min at 2000 g. PVD explants in groups of 30 were tested with either 10% Noni, 10% protein-free Noni, or control HPVAM with an equivalent amount of saline. These data showed that removal of protein did not diminish the effect of the Noni juice on the inhibition of the initiation and proliferation of angiogenesis. (FIG. 8). This is evidence that the antiangiogenic factor in Noni juice is not a protein.

Extraction by Molecular Weight: Noni juice was dialyzed in 20 ml aliquots against 8 L of isotonic saline (NaCl), using Spectrapor dialysis bags (Spectrum Medical Industries, Houston, Tex.) with molecular weight cutoffs of 1 kD, 3.5 kD, 25 kD, and 50 kD. The solutions remaining in all dialysis bags were effective in reducing the angiogenic initiation and in inhibiting angiogenic growth when tested on PVD. (Data not shown). Although these data suggested that a major antiangiogenic agent in Noni juice had a molecular weight greater than about 50 kiloDaltons, subsequent experiments indicated that a primary antiangiogenic ingredient in fact had a molecular weight less that 6000 Daltons. Evidently, either the carbohydrate fraction did not dialyze in the Spectrapor dialysis bags according to molecular weight as would proteins, or another antiangiogenic component with a molecular weight greater than about 50 kD can be found in Noni juice.

Carbohydrate Oxidation by Sodium (meta) Periodate: Noni juice (20 ml) was combined with 0.2 g of sodium (meta) periodate, a known selective oxidizing agent of carbohydrates (See R. T. Morrison and R. N. Boyd, Organic Chemistry, 3rd Edition, Allyn and Bacon, Inc., p. 538 (1974)), and kept overnight in the cold (4° C.) with stirring. The resultant mixture was adjusted to pH 7.4 with 50% NaOH and diluted in Media 199 to give an equivalent concentration to that of 10% Noni juice. The resulting solution was tested on PVD explants. As controls, two groups of PVDs were treated either with 10% saline or with 10% Noni juice.

Figure 9A:
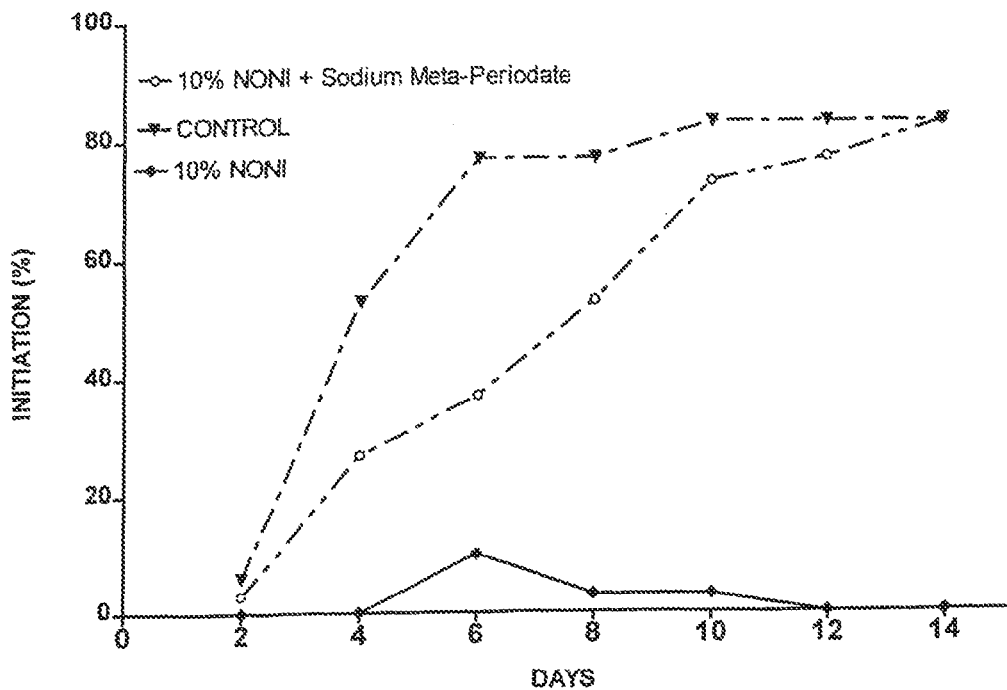
FIG. 9a illustrates the effect on angiogenic initiation of selective oxidation of carbohydrates in Noni juice by treatment with sodium meta periodate.
Figure 10A:
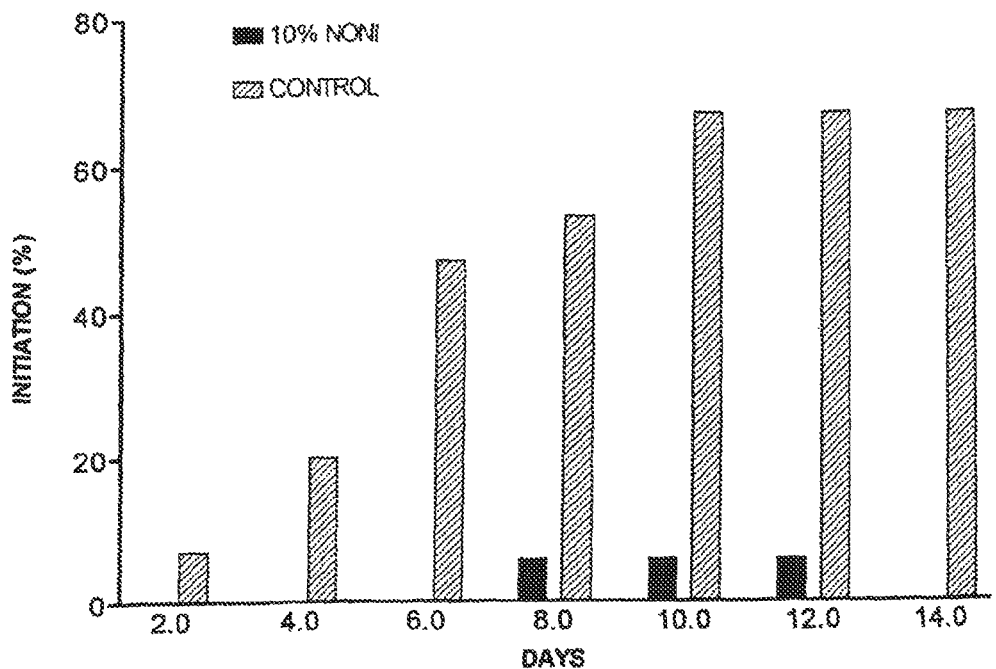
FIG. 10a illustrates the effect of 10% Noni juice on the initiation of angiogenesis in human breast cancer explants.
Figure 10B:
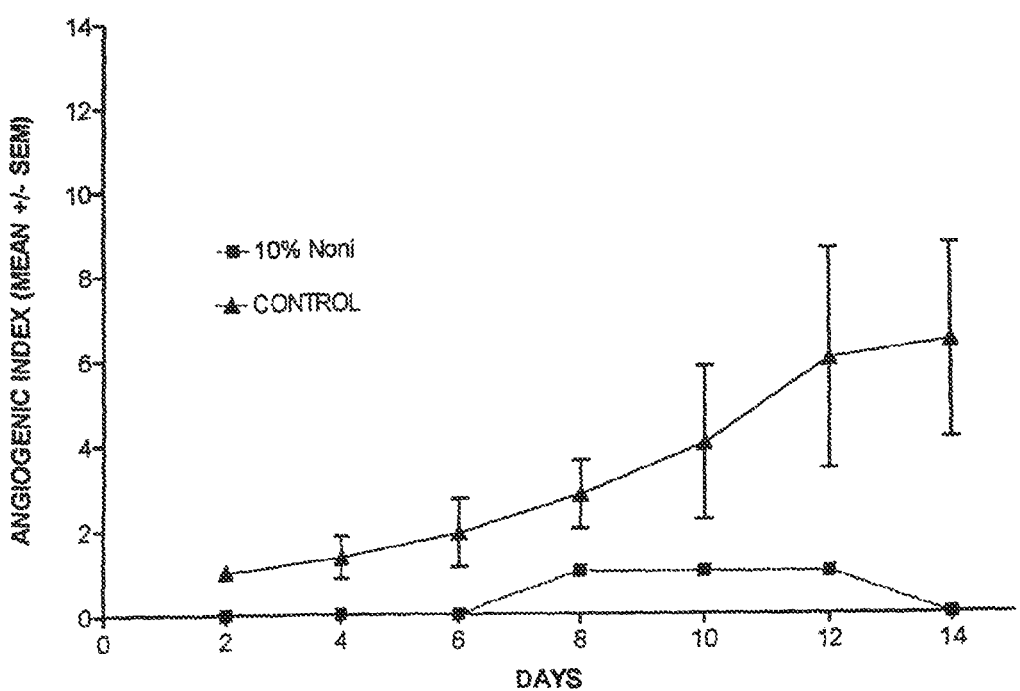
FIG. 10b illustrates the effect of 10% Noni juice on the initiation and proliferation of angiogenesis in human breast cancer explants as measured by an angiogenic index.

As shown in FIG. 9a, 10% Noni juice treated with sodium (meta) periodate lost the ability to inhibit initiation of angiogenesis. This result suggests that the factor in Noni juice that inhibits initiation of angiogenesis is a carbohydrate whose oxidation by sodium metaperiodate was sufficient to render the factor ineffective in inhibiting angiogenic initiation.

Figure 9B:
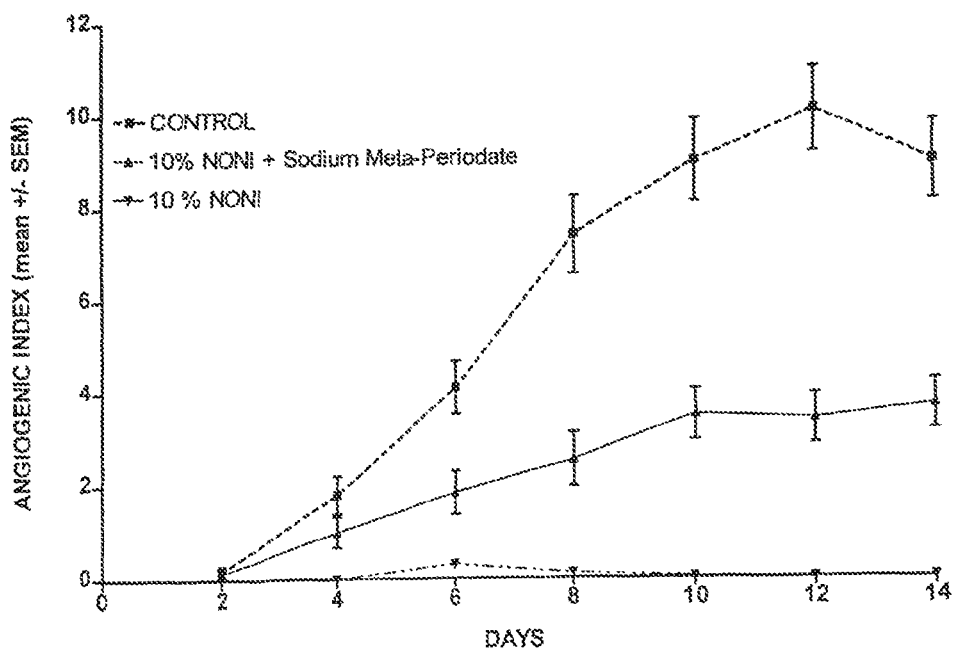
FIG. 9b the effect on angiogenic growth and proliferation of selective oxidation of carbohydrates in Noni juice by treatment with sodium meta periodate.

However, the oxidation of 10% Noni juice sodium (meta) periodate only partially reduced (by 60%) the ability of Noni juice to inhibit angiogenic growth and proliferation. (FIG. 9b). This result suggests that the inhibition of angiogenic proliferation by Noni juice may result at least in part from a different factor, perhaps a non-carbohydrate factor. Alternatively, the structural change of the active carbohydrate factor that rendered the factor ineffective in inhibiting angiogenic initiation may have been insufficient to render the same factor totally ineffective in inhibiting angiogenic proliferation.

EXAMPLE 9

Effect of Noni Juice Concentrate on Psoriasis

To test the effectiveness of a Noni juice concentrate on psoriasis, patients were selected at the Louisiana State University Health Science Center (LSUHSC) after signing a consent form approved by the LSUHSC Institutional Review Board. All patients were asked to continue using whatever therapy they had been using for the psoriasis. Each patient was given two distinct 8 gm jars of a gel, one a gel with Noni and one a control gel. The jars did not indicate which contained the Noni juice. The patients were randomly divided on which arm (right or left) would be treated with the Noni gel, with the other arm treated with the control gel. The patients were asked to treat the affected area topically twice a day. Pre-study photographs of psoriatic lesions on the Noni-treated and control-treated extremities were taken. Patients were monitored and photographed weekly or bi-weekly. Patients were also asked to rate the condition of their skin. An unbiased observer was asked to rate the lesions or plaques on the skin, using a 9-point grading system. The 9-point grading system was the sum of a grade of 0 to 3 for each of three categories—erythema, scale, and elevation.

Noni juice gel was prepared by freeze-drying Noni juice into a powder. The powder was compounded into a gel at a concentration of about 20% wt/vol, by initially using rosewater in a volume equal to two-thirds of the total to attempt to camouflage the pungent odor of Noni. Then Krisgel liquid, cellulose hydroxy propyl ether (Professional Compounding Centers of America, Houston, Tex.), was added to bring the volume to the final total, and the combination was mixed until it gelled. The control was the same rosewater/Krisgel liquid mixture without the Noni.

To date, six patients have been studied. All six patients reported that the Noni-containing gel had an unpleasant smell and stained the skin a brown color that was easily removed with soap and water. All six patients felt that plaques treated with Noni showed improvement. As rated by the patients, the total score for the Noni arm decreased by 3.6, while the score for the other arm only decreased by 0.5. As rated by the independent observer, the total score for the Noni arm decreased by 3.1 in the Noni-treated arm, while the score for the other arm only decreased by 0.2.

This experiment showed that Noni juice applied topically as a gel was effective in treating skin lesions associated with psoriasis in humans.

In similar experiments, Noni juice or an angiogenic extract will be tested for effectiveness of a topical administration against other skin disorders that involve angiogenesis, e.g., Kaposis sarcoma and some skin cancers.

EXAMPLE 10

Effectiveness of Noni Juice on Angiogenesis in Breast Cancer Explants

Explants from human breast cancer tissue were obtained from an anonymous discarded surgical specimen under the approval of an Institutional Review Board. The cancer tissue came from a tumor with a size greater than 1 cm3. Cubes of about 2 mm on each side were excised and plated in well plates. The explants were treated with Medium 199 supplemented with 20% fetal bovine serum and either 10% NaCl (control) or 10% Noni juice. The medium in each well was changed, and the discs scored every two days.

Noni juice was very effective in suppressing angiogenic initiation (FIG. 10a), and in inhibiting angiogenic proliferation (FIG. 10b) in the breast cancer explants.

EXAMPLE 11

Treatment of Proliferative Retinopathies by Noni Juice or an Extract of Noni Juice To test the effectiveness of Noni juice or an antiangiogenic extract of Noni juice, patients with symptoms of proliferative retinopathies, e.g., diabetic retinopathy, will be divided into two groups. One group will receive a placebo; and the other Noni juice or an active extract of Noni juice, administered either by injection or orally in a tablet form, per os. The treatment will be administrated during prolonged periods of time after disease onset to inhibit pathological neovascularization. The degree of neovascularization will be followed using standard methods to measure vascularization in the eye. The treatment with Noni juice or an angiogenic extract of Noni juice will result in a decrease in the degree of preexisting vascularization and prevent the development of new angiogenic vessels.

EXAMPLE 12

Effect of Oral versus Intraperitoneal Administration on Antiangiogenic Activity

To test whether oral administration and subsequent digestion would allow the active extract in Noni juice to appear in the blood plasma, an experiment was conducted using adult Sprague-Dawley rats. Noni juice was freeze-dried and then reconsititued with distilled water. The rats were divided into five groups with six rats in each group. Each group was assigned one of the following treatments: (1) a control (no treatment); (2) daily gavage of 200 mg of freeze-dried Noni juice in 1 ml dH2O; (3) daily gavage of 400 mg of freeze-dried Noni juice in 1 ml dH2O; (4) daily injection of 200 mg of freeze-dried Noni juice in 1 ml dH2O; and (5) daily injection of 400 mg of freeze-dried Noni juice in 1 ml dH2O. Each rat was given the same treatment for three days. One hour after the last treatment, the rats were killed and bled. The blood was centrifuged to separate the cells from the serum The serum was then used in the human placental vein angiogensis model (See Example 1) to assay for initiation of angiogenesis. The discs were treated with 0.2 ml with one of six solutions: (1) medium with 20% fetal bovine serum (FBS); (2) medium with 10% FBS/10% serum from a control rat; (3) medium with 10% FBS/10% serum from a rat orally given 200 mg Noni; (4) medium with 10% FBS/10% serum from a rat orally given 400 mg Noni; (5) medium with 10% FBS/ 10% serum from a rat injected with 200 mg Noni; and (6) medium with 10% FBS/10% serum from a rat injected with 400 mg Noni. The discs were checked on Days 6, 8, 11, and 13 for angiogenic activity. Only serum from the rat that received the intraperitoneal injections of 400 mg indicated any inhibition of angiogenesis. All other treatments were not significantly different from the controls. (Data not shown)

These preliminary results indicate that oral administration of Noni juice may not be effective as antiangiogenic therapy at doses that are reasonable. The effectiveness of oral injestion of the active antiangiogenic component will be tested. The Noni juice or its active extract may have to be given systemically or intraperitoneally to be effective. Alternatively, the active Noni component(s) could be given orally if packaged to protect from digestion by methods known in the art.

EXAMPLE 13

Further Characterization of an Active Fraction from Noni Juice

In order to isolate the active component from Noni juice, the 100% juice was brought to pH 7.4 with 50% NaOH, centrifuged overnight at 130,000 gav, and lyophilized. The pellet was reconstituted in deionized, distilled water (ddH2O) to a volume about half of the original juice, filtered through a 0.2 micron filter, and fractionated on a Sephacryl S-200 column with ddH2O with a flow rate of 0.17 ml/min. From this column, 160 fractions of 3 ml each were collected. The fractions were pooled in groups of five and tested against Human umbilical vein endothelial cells (HUVEC) for their ability to inhibit endothelial cell growth.

The HUVEC assay is faster than the human placental vein angiogenesis model (HPVAM). The HUVEC assay used human umbilical vein endothelial cells purchased from the American Type Culture Collection (ATCC #CRL-1730, Manassas, Va.). HUVEC cells in exponential growth phase were harvested from tissue culture flasks and plated in a 96-well plate at a density of 2,000 cells/well in 0.2 ml growth medium as described in J. C. Watson et al., "Growing vascular endothelial cells express somatostatin subtype 2 receptors," Br. J. Cancer, vol. 85, pp. 266-272 (2001). Alternatively, the cells were grown in 0.2 ml growth medium supplemented with the pooled sample from the column. Cell growth and viability was determined using an MTT assay (Promega, Madison Wis.). The more active pooled samples inhibited cell growth and increased cell mortality.

Following identification of the most active fractions using HUVEC, the fractions were tested for antiangiogenic activity in the Human Placental Vein Angiogenesis Model (HPVAM) as described in Example 1. The most active pooled fraction was from the 3 ml fractions numbered 56 through 60. This pooled sample was given the designation "f-6". The data in Table 1 show the activity of this f-6 pooled fraction in the HPVAM model. Initiation of new angiogenic growth was inhibited by more than 90% by this fraction, while growth and proliferation (Angiogenic Index) remained negligible. All wells (including those scored as zero) are included in the following analysis.

TABLE 1

|  | DAY 2 | DAY 7 | DAY 14 |
|---|---|---|---|
| A. Initiation (Mean from 3 Placentas) | | | |
| CONTROL (n = 55) | 0 | 58% | 72% |
| f-6 (n = 50) | 0 | 10% | 9% |
| B. Growth and Proliferation in Angiogenic Index (Mean from 3 Placentas) | | | |
| CONTROL (n = 55) | 0 | 2.4 | 8.5 |
| f-6 (n = 50) | 0 | 0.4 | 0.1 |

EXAMPLE 14

Identification of Composition of Fraction "f-6"

The active fraction f-6 isolated as in Example 13 has been partially characterized. Briefly, the methods used were as follows. Size exclusion chromatography was performed on a portion of the f-6 sample by preparing a solution using distilled H2O and injecting an aliquot onto a P-6 gel column, connected to a refractive index detector, at a flow rate of 0.12 ml/min using deionized, degassed water as the eluent. The P-6 column has an exclusion limit of 6000 daltons. The sample was collected with the fractions representing individual peaks being pooled for methyl glycoside analysis. In this sample, four peaks were identified.

Methyl glycosides were prepared from the four peaks collected from the P-6 runs by the following method: Methanolysis in 1M HCl in methanol at 800 C (18-22 hours) was followed by r-N-acetylation with pyridine and acetic anhydride in methanol for the detection of amino sugars. The samples were then per-O-trimethylsilylated (TMS) by treatment with Tri-Sil (Pierce) at 800 C (0.5 hours). These procedures were as previously described by W. S. York et al., Methods Enzymol., vol. 118, pp. 3-40 (1985). GC/MS analysis of the TMS methyl glycosides was performed on an Hewlett Packard 5890 GC interfaced to a 5970 MSD, using a Supelco EB5 fused silica capillary column. An internal standard (myo-inositol, 20 µg to each sample) was added prior to derivatization.

The results from size exclusion chromatography revealed that the sample contained four (4) peaks, each which eluted at a retention time that indicated a molecular weight of less than about 6000 Daltons.

The results of the glycosyl composition analysis for each peak are given in Table 2. (The data for the combined GC/MS from the TMS procedure are not shown.) The monosaccharides were identified by their retention times in comparison to the standards, and the carbohydrate character of the compounds was confirmed by their mass spectra.

TABLE 2

Glycosyl Composition Analysis

| Sample | Molar % | Glycosyl Residue | Weight (µg) |
|---|---|---|---|
| Peak 1 | 2.0 | Rhamnose | 0.4 |
|  | 1.9 | Xylose | 0.3 |
|  | 52.0 | Galacturonic acid | 11.8 |
|  | 8.0 | Mannose | 1.7 |
|  | 21.2 | Glucose | 4.5 |
|  | 14.9 | Unknown sugar | 3.2 |
| Peak 2 | 11.4 | Galacturonic Acid | 0.7 |
|  | 5.4 | Mannose | 0.3 |
|  | 60.3 | Glucose | 3.2 |
|  | 23.0 | Unknown sugar | 1.2 |
| Peak 3 | 0.4 | Rhamnose | 0.3 |
|  | 16.1 | Galacturonic acid | 10.7 |
|  | 2.2 | Galactose | 1.4 |
|  | 60.4 | Glucose | 37.3 |
|  | 20.9 | Unknown sugar | 12.9 |
| Peak 4 | 0.4 | Rhamnose | 0.3 |
|  | 5.8 | Glucuronic acid | 1.0 |
|  | 42.8 | Glacturonic acid | 7.5 |
|  | 29.2 | Glucose | 4.7 |
|  | 20.5 | Unknown sugar | 3.3 |

Size exclusion chromatography showed that the active fraction (f-6) was composed mainly of low molecular weight compounds. The higher molecular weight components eluted first on the P-6 column and are in Peak 1. The lower molecular weight components are in peak 4. Separation of f-6 on the P-6 column indicated that this fraction did not contain any amino sugars when a methyl glycoside analysis was performed. A better separation was obtained with the P-6 column than with the Superdex-12 column used earlier (Data not shown). The active fraction (f-6) was mainly a mixture of residues of glucose, galacturonic acid, and unknown sugar residues. These three sugars constituted 88%, 95%, 96%, and 92% by molar percent of the total of Peaks 1, 2, 3, and 4, respectively. Moreover, these four peaks contained by molar % between about 65% and 80% galacturonic acid and glucose. A combination of NMR and further MS analysis will be used for further characterization of the components.

We will test each of the four peaks for antiangiogenic activity by the method described above in Example 1. Moreover, as the individual sugars are identified, they will also be tested for antiangiogenic activity. It is expected that one or more of the four peaks will have antiangiogenic activity, and that either galacturonic acid or the unknown sugars or both may show antiangiogenic activity.

Miscellaneous

The term "therapeutically effective amount" as used herein refers to an amount of the Noni juice or an extract of Noni juice or an active factor(s) from Noni juice sufficient either to inhibit angiogenesis or to degrade existing capillary networks to a statistically significant degree (p<0.05). The term "therapeutically effective amount" therefore includes, for example, an amount sufficient to prevent the growth of angiogenic vessels found in diseases of tumor growth, diabetic retinopathy, psoriasis, retinopathy of prematurity, and preferably to reduce by at least 50%, and more preferably to reduce by at least 90%, the amount of angiogenesis. The dosage ranges for the administration of the Noni juice or its active extract are those that produce the desired effect. Generally, the dosage will vary with the age, weight, condition, sex of the patient, type of tumor or other pathology, the degree of tumor development, and the degree of angiogenic response. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of angiogenic inhibition or remission by methods well known to those in the field. Moreover, the Noni juice or its active extract can be applied in pharmaceutically acceptable carriers known in the art. The Noni juice or its extract can be used to treat cancers in animals and in humans in vivo. The application can be oral, by injection, or topical, providing that in an oral administration the Noni juice or extract is preferably protected from digestion.

Noni juice or an active extract may be administered to a patient by any suitable means, including parenteral, subcutaneous, intrapulmonary, topically, and intranasal administration. Parenteral infusions include intramuscular, intravenous, intraarterial, intraperitoneal administration. Additionally, the infusion could be into an organ. Injection of Noni juice or its active extract may include the above infusions or may include intraperitonieal, intravitreal, direct injection into a tumor, or direct injection into a site of angiogenic disease. Noni juice or an active extract may also be administered transdermally, for example in the form of a slow-release subcutaneous implant, or orally in the form of capsules, powders, or granules. Although direct oral administration seems to cause loss of antiangiogenic activity, the Noni juice or its extract could be packaged in such a way to protect the active ingredient(s) from digestion by use of enteric coatings, capsules or other methods known in the art.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, and glycerol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

Noni juice or an active extract of Noni juice may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the Noni juice or active extract may be controlled by altering the concentration of the macromolecule.

Controlled delivery can also be achieved by conjugating the active ingredient of the Noni juice with a known compound that targets cellular surface receptors that are known to be unique to angiogenic blood vessels, e.g., somatostatin and its analogs and derivatives (binding to somatostatin receptor subtype 2), platelet-derived growth factor (binding to platelet derived growth factor receptor), and vascular endothelial growth factor(binding to a kdr receptor). See M. O. Meyers et al, "Gene upregulation of PDGF in human angiogenesis," abstract presented at Association for Academic Surgery, 1998; J. C. Watson et al., "SST-2 gene expression appears during human angiogenesis," abstract published in Regul. Peptide, vol. 64, pp. 206 (1996); J. C. Watson et al., "Initiation of kdr gene transcription is associated with conversion of human vascular endothelium to an angiogenic phenotype," Surgical Forum, vol. 47, pp. 462-464 (1996); and J. C. Watson et al., "Growing vascular endothelial cells express somatostatin subtype 2 receptors," British Journal of Cancer, vol. 85, pp. 266-272 (2001).

Another method for controlling the duration of action comprises incorporating the Noni juice or an active extract into particles of a polymeric substance such as a polyester, peptide, hydrogel, polylactide/glycolide copolymer, or ethylenevinylacetate copolymers. Alternatively, Noni juice or an active extract may be encapsulated in microcapsules prepared, for example, by coacervation techniques or by interfacial polymerization, for example, by the use of hydroxymethylcellulose or gelatin-microcapsules or poly (methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The present invention provides a method of preventing, treating, or ameliorating a disease that causes an angiogenic response in the body such as tumors, retinopathy, and psoriasis, comprising administering to a subject at risk for a disease or displaying symptoms for such disease, a therapeutically effective amount of Noni juice or an active extract of Noni juice. The term "ameliorate" refers to a decrease or lessening of the symptoms or signs of the disorder being treated. The symptoms or signs that may be ameliorated include those associated with an increase in angiogenesis in the body.

The complete disclosures of all references cited in this specification are hereby incorporated by reference. In the event of an otherwise irreconcilable conflict, however, the present specification shall control.

What is claimed is:

1. A method of treating psoriasis in a mammal in need thereof, said method comprising topically administering to the mammal a Noni juice gel formulation comprising a therapeutically effective amount of an extract of Noni juice that is an alcohol precipitate of Noni juice free of carbohydrates of a molecular weight greater than 6000 daltons as determined by size exclusion chromatography; wherein the extract of Noni juice is administered in a concentration from about 10% to about 20% weight/volume of the Noni juice gel.

2. The method of claim 1, wherein said mammal is a human.

3. An alcohol extract of Noni juice, wherein said extract is an alcohol precipitate of Noni juice free of carbohydrates of a molecular weight greater than 6000 daltons as determined by size exclusion chromatography.

* * * * *